US012648769B2

(12) United States Patent　　　　(10) Patent No.:　US 12,648,769 B2
Yost et al.　　　　　　　　　　　　(45) Date of Patent:　　　Jun. 9, 2026

(54) TIE SYSTEMS FOR STERNAL CLOSURE

(71) Applicant: THE REGENTS OF THE UNIVERSITY OF MICHIGAN, Ann Arbor, MI (US)

(72) Inventors: Gardner Yost, Ann Arbor, MI (US); Jeffrey Stephen Plott, Algonac, MI (US); Jonathan Haft, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 860 days.

(21) Appl. No.: 17/909,953

(22) PCT Filed: Mar. 9, 2021

(86) PCT No.: PCT/US2021/021522

§ 371 (c)(1),
(2) Date: Sep. 7, 2022

(87) PCT Pub. No.: WO2021/183524

PCT Pub. Date: Sep. 16, 2021

(65) Prior Publication Data

US 2023/0107886 A1　　　Apr. 6, 2023

Related U.S. Application Data

(60) Provisional application No. 62/987,088, filed on Mar. 9, 2020.

(51) Int. Cl.
A61B 17/04　　　　(2006.01)
A61B 17/06　　　　(2006.01)

(52) U.S. Cl.
CPC ...... A61B 17/0401 (2013.01); A61B 17/0487 (2013.01); A61B 17/06 (2013.01); (Continued)

(58) Field of Classification Search
CPC ........ A61B 17/0401; A61B 2017/0403; A61B 2017/0404; A61B 2017/0406; (Continued)

(56) References Cited

U.S. PATENT DOCUMENTS

| | | | |
|---|---|---|---|
| 5,643,295 | A | 7/1997 | Yoon |
| 6,033,429 | A | 3/2000 | Magovern |

(Continued)

FOREIGN PATENT DOCUMENTS

| | | | | |
|---|---|---|---|---|
| EP | 1080693 A1 | * | 3/2001 | ........... A61B 17/823 |

OTHER PUBLICATIONS

International Application No. PCT/US21/21522, International Search Report and Written Opinion, dated May 25, 2021.

(Continued)

*Primary Examiner* — Larry E Waggle, Jr.
(74) *Attorney, Agent, or Firm* — MARSHALL, GERSTEIN & BORUN LLP

(57)　　　　　ABSTRACT

A sternal tie assembly having a pair of hook-shaped needles, a length of sternal tie extending from a proximal end of each of the needles, and a pair of posterior plugs, each of the posterior plugs being slidably mounted on the tie and tethered, via suture material, to the proximal end of a respective one of the needles. A method of use of the sternal tie assembly includes creation of a hole or channel in sternum, manubrium, rib, rib cartilage, intercostal muscle, or other tissue, drawing a portion of the tie and the suture material through the channel formed in the tissue by the needle, severing the needle from the tie and suture material, continuing to advance the suture material until a post of each of the posterior plugs is pulled into the respective channel in the tissue, or at least until a head of the plug is disposed against the channel in the tissue, then threading an anterior plug onto each exposed end of the sternal tie, securing the anterior plugs into respective anterior openings in the tissue, then crossing and twisting the sternal tie ends together until the tissue ends are closed together.

24 Claims, 27 Drawing Sheets

(52) U.S. Cl.
CPC ................. *A61B 2017/0404* (2013.01); *A61B 2017/0406* (2013.01); *A61B 2017/0409* (2013.01); *A61B 2017/0412* (2013.01); *A61B 2017/0414* (2013.01); *A61B 2017/0445* (2013.01); *A61B 2017/0456* (2013.01); *A61B 2017/0495* (2013.01); *A61B 2017/06057* (2013.01); *A61B 2017/06176* (2013.01)

(58) Field of Classification Search
CPC .... A61B 2017/0408; A61B 2017/0412; A61B 2017/0414; A61B 2017/0445; A61B 2017/0456; A61B 2017/047; A61B 2017/048; A61B 17/06; A61B 2017/06057; A61B 2017/06176; A61B 17/823
See application file for complete search history.

(56) References Cited

U.S. PATENT DOCUMENTS

| | | | |
|---|---|---|---|
| 6,059,818 A | | 5/2000 | Johnson et al. |
| 6,302,899 B1 | | 10/2001 | Johnson et al. |
| 6,506,197 B1 | | 1/2003 | Rollero et al. |
| 8,062,295 B2 | | 11/2011 | McDevitt et al. |
| 8,323,338 B2 | * | 12/2012 | LeBeau .............. A61B 17/0401 |
| | | | 623/13.12 |
| 2003/0078585 A1 | | 4/2003 | Johnson et al. |
| 2004/0116963 A1 | * | 6/2004 | Lattouf .............. A61B 17/0469 |
| | | | 606/224 |
| 2011/0066185 A1 | | 3/2011 | Wotton, III |
| 2013/0345745 A1 | | 12/2013 | Kim |
| 2015/0051697 A1 | | 2/2015 | Spence et al. |

OTHER PUBLICATIONS

European Patent Application No. 21766882.1, Extended European Search Report, dated Nov. 2, 2023.

* cited by examiner

Pass needle through sternum or intercostal muscle, from posterior to anterior - Left side

Pass needle through sternum or intercostal muscle, from posterior to anterior - Right side

Slide posterior plugs into needle hole on posterior side of sternum.

Cut needles free from wire and suture.

Slide anterior plug onto wire and into hole on anterior side of sternum.

Tie suture material tightly over top of anterior plugs

Tighten sternal wires to bring together and affix the sternal halves.

FIG. 18

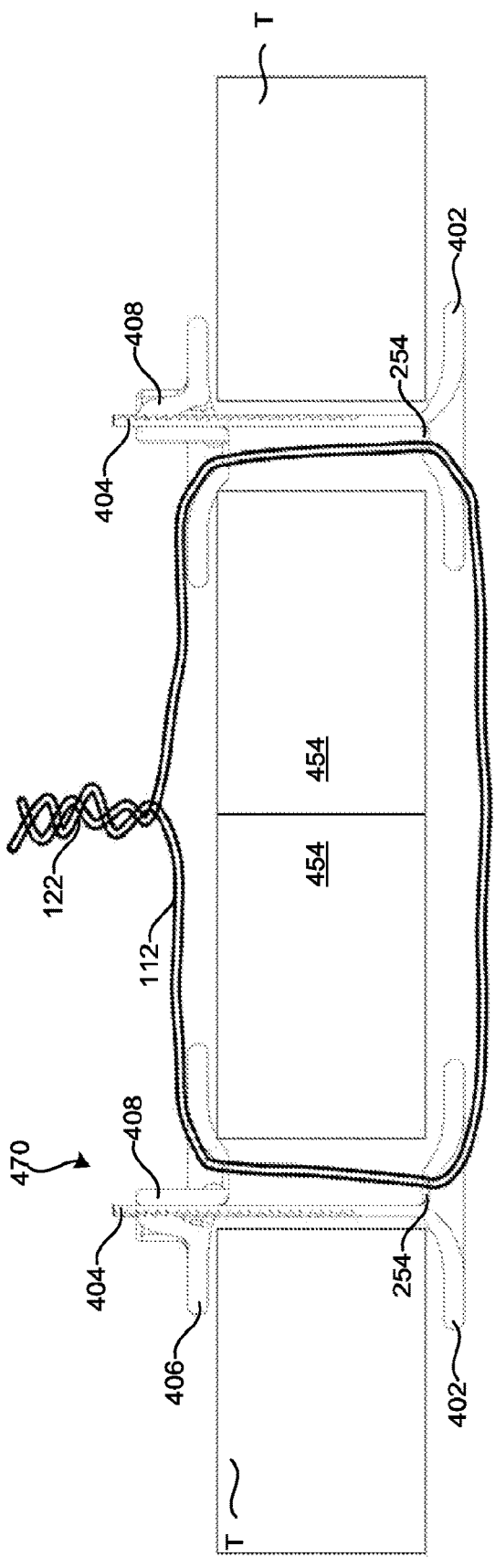
FIG. 30A

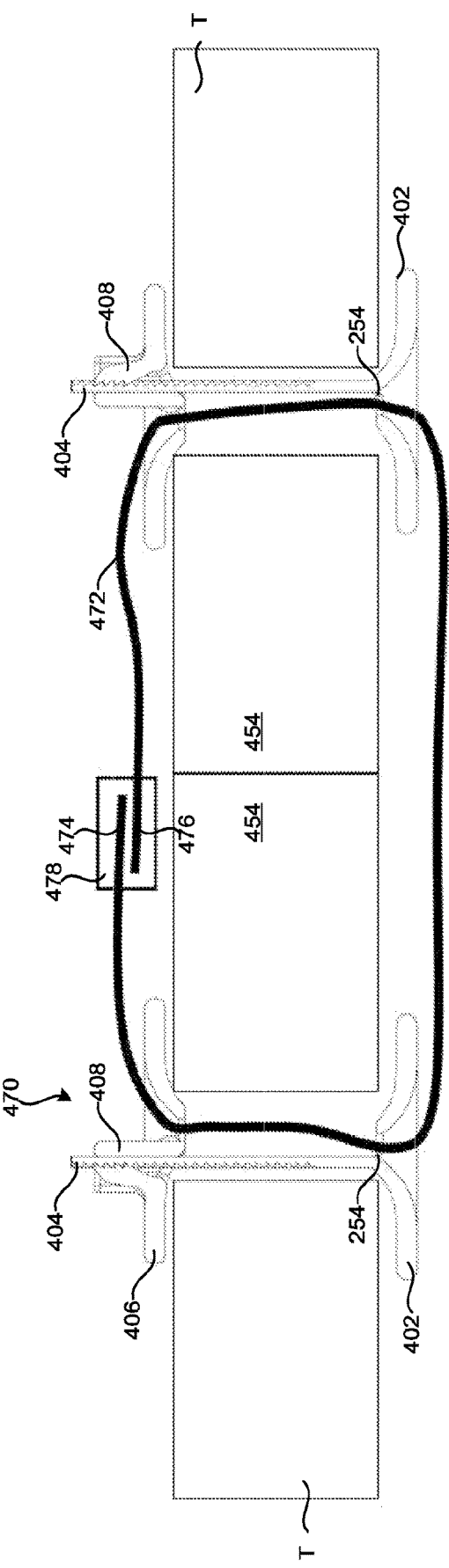

TIE SYSTEMS FOR STERNAL CLOSURE

CROSS-REFERENCE TO RELATED APPLICATIONS

This application is a 35 U.S.C. § 371 National Stage of International Application PCT/US21/21522, filed Mar. 9, 2021, which claims priority to U.S. Provisional Application No. 62/987,088, filed Mar. 9, 2020, the content of each of which is incorporated by reference herein in their entireties and for all purposes.

FIELD OF THE DISCLOSURE

The present disclosure relates generally to improved medical devices and techniques for performing tie cerclage closure of the sternum.

BACKGROUND

Wire cerclage closure is, by far, the most common means for sternal re-approximation. Despite this, sternal wires can cause bleeding from needle holes and can exert excess force on the sternal bone over time, resulting in non-union or dehiscence. These complications can necessitate prolonged operative times, re-operation, blood product administration, and increased levels of care.

Wire cerclage is a simple, inexpensive, and practical means of sternal re-approximation, and, importantly, permits expeditious re-entry into the mediastinum in the case when emergent exploration is required. Several studies utilizing large multicenter cohorts of patients undergoing cardiac surgery with sternotomy have demonstrated that reoperation for excessive bleeding occurs in 5-9% of cases. Poorly controlled sternal bleeding is a common culprit in excessive post-operative bleeding. This may be due to oozing from the sternal incision or the opening of an artery or vein after sternal closure, but often is a result of passage of sternal wires through the bony and soft tissues of the chest. The holes created by the needles and sternal wires are large and are prone to bleeding, as the sternum is a well vascularized area. Some surgeons will attempt to address this bleeding by applying hemostatic agents into the needle holes to attempt to achieve both local tamponade and coagulation. Another approach for ongoing sternal wire bleeding is placement of a compressive suture around each needle hole. This approach is laborious and time-consuming. In addition to the problem of bleeding from needle holes, the use of sternal wires can lead to sternal malunion or dehiscence. This is most often a result of compression of the manubrium or sternal edges by taut stainless-steel wires which erode through the bone over time, leading to loosening and separation of the sternal edges. Sternal malunion is a disfiguring complication, results in significant discomfort, and can compromise respiration. Dehiscence, often complicated by infection, requires surgical intervention in an attempt to reapproximate the sternum. This is a highly morbid complication, and yet the most common solution is reuse of sternal wires to create a woven wire matrix surrounding the sternum and ribcage.

Competing technologies include the sternal wire as currently utilized. This is considered the gold standard. An important barrier to commercialization is potential hesitance of the surgeon to adopt a new device which requires additional time and effort to use. A newer device for sternal closure is the sternal plate, which utilizes titanium plates screwed onto the superficial surface of the sternum. While sternal plating systems have been shown to reduce rates of sternal malunion, they have several drawbacks including cost, time to implement, and difficulty to rapidly re-enter the chest after the sternal plate is secured. Other closure strategies include braided sternal wires and bands which are tightened in a fashion similar to zip-ties.

The use of hollow anchor mechanisms to facilitate wire closure of severed bone and other tissue has been disclosed. Examples include the teachings of U.S. Pat. Nos. 6,033,429, 6,059,818, and 6,302,899 of Cardiac Assist Technologies, Inc. These patents disclose the use of hollow barbed anchors or grommets in severed bone and the subsequent threading of stainless-steel wire or suture material through the bore of each of the anchors or grommets to serve as a lash to close the severed bone and other tissue. Each of these disclosures contemplates a separate instrument in the form of a placing mechanism employed to deploy the anchors or grommets into the bone or other tissue. At the time of deployment, the anchors or grommets are not in communication with wire or suture material. Such a separate placing mechanism suffers from several drawbacks, such as the risk of one or more of the small untethered anchors or grommets falling loose from the placing mechanism, or prematurely dislodging from the bone or other tissue, and becoming lost inside the patient. Given the sharp barbs provided to enhance securement of the anchors or grommets, and the close proximity to critical vessels and organs, this risk is of significant concern. Additionally, the need for a separate applicator represents an inconvenience to the surgeon, additional expense, sterilization challenge, and introduces new technical difficulty as there is limited space for maneuvering of the instruments in the thoracic cavity.

Another drawback of such disclosed placing mechanisms is that placing mechanisms which contemplate deployment of both posterior and anterior anchors or grommets, the bores of such posterior and anterior anchors/grommets are, once deployed, coaxial with one another, posing a practical challenge of threading a sternal wire through small coaxial openings using a C-shaped (or hook-shaped) needle. Alternatively, if a straight needle is employed to thread the sternal wire through the coaxial openings of the posterior and anterior anchors or grommets, manipulating such a straight needle requires application of large forces, great dexterity and risks causing additional bleeding due to the limited space behind the anterior thoracic wall to accommodate the length of the needle.

Certain of the disclosed anchors or grommets require crimping in order to ensure securement in the bone or other tissue, which detrimentally requires the use of yet an additional crimping instrument, thereby prolonging the duration of the surgery.

U.S. Pat. No. 8,062,295, to McDevitt (DePuy Mitek, Inc.), discloses the use of a hollow cylinder, which the patent refers to as an "eyelet," that is secured with suture material, interference fit, or surgical epoxy, into a transosseous tunnel, for use in rotator cuff reconstructive surgery.

The manner in which the above drawbacks, and others, in the prior art can be overcome by the constructions and techniques of the present disclosure are detailed below.

SUMMARY OF THE DISCLOSURE

The present disclosure relates to sternal tie systems incorporating hemostatic, force distributing elements. There is a need for a system that reduces both blood loss from sternal needle holes and rates of sternal dehiscence as a result of bone cutting, as such a system would shorten operative times, improve aggregate patient outcomes, and reduce surgical and post-surgical costs.

The device of the present disclosure utilizes a plug, having a hollow post or stem that may or may not be barbed or provided with tangs, which is fed into a needle hole in the sternum around a length of sternal tie. By advancing the plug into the needle hole, there is tamponade of bleeding around that hole, particularly as the tie is tightened. Under normal circumstances there is direct abutment of the tightened tie against the boney surface. This plug device advantageously distributes the forces applied by the tie onto a larger surface area of bone. This should reduce rates of tie erosion into bone and maintain long-term sternal approximation. Return to the operating room confers additional risk to the patient in the form of anesthesia, mechanical ventilation, re-do sternotomy, and potential re-utilization of cardio-pulmonary bypass. There is also increased need for red blood cell and coagulation factor transfusion as well as other intravenous medications which target hemostasis and blood pressure control. Not surprisingly, the mortality rate in these patients is appreciably higher compared to patients who need no additional surgical intervention. There are other costs which must be considered: the emotional costs to the family and the caregivers exacted by a return to the operating room as well as the financial costs of running and staffing an additional operating room and providing increased non-surgical therapy. It is assumed that use of this device, by reducing volume of post-closure blood loss and improving long-term stability of the tie reinforced sternum, will result in lower rates of re-operation.

The sternal tie assembly of the present disclosure includes at least one needle, preferably C-shaped or hook-shaped, having a sharp distal end capable of piercing and penetrating hard and semi-hard tissue, including one or more of sternum, manubrium, ribs, rib cartilage, and intercostal muscle and a proximal end from which a length of sternal tie extends. Also extending from a proximal end of the needle is suture material, preferably in the form of at least two suture lines each being secured at a first end to the proximal end of the needle and at a second end to a head of a posterior plug. The posterior plug is provided with a hollow post or stem, the bore through the axis of the post or stem extending through the head of the posterior plug. The posterior plug is slidably mounted along the sternal tie, with the post or stem facing the proximal end of the needle. In one embodiment, the posterior plug has a plurality of suture-receiving holes through the head, which are occupied by the suture lines to tether the posterior plug to the proximal end of the needle.

In a preferred embodiment, the sternal tie assembly is provided with two needles, one on either end of the sternal tie, each of the needles having a respective posterior plug slidably received on the sternal tie and tethered to the proximal end of that needle by suture material.

In use, the assembly is removed from a sterile package, and a distal end of each of the needles is inserted through respective exposed sternum, manubrium, rib, rib cartilage, intercostal muscle, or other tissue that has been separated for an invasive surgical procedure, such as a sternotomy. In a preferred use, the needles are inserted from a posterior side of the tissue toward an anterior side, but insertion of one or both of the needles is within the scope of the present disclosure. After each needle is advanced through the respective tissue, forming a hole through the tissue, the hole is immediately occupied by the sternal tie and suture material extending from the proximal end of the needle. Inasmuch as both needle sides are manipulated in the same manner, for ease of description, only one needle side is discussed in the following steps, but it is to be understood that the same operations are to be performed on both sides of the separated sternum, manubrium, rib, rib cartilage, intercostal muscle, or other tissue. The needle, tie, and suture material are continually advanced past the tissue until the post or stem of the respective posterior plug is nearly drawn into the hole through the tissue.

Next, the needle is severed from the sternal tie and suture material. After removal of the needle, the suture material is pulled to further advance the post or stem of the posterior plug into the hole (formed by the needle) through the tissue. Next, an anterior plug, also having a hollow post or stem, the bore of which extending through an open head of the anterior plug, is threaded, leading with its post or stem, along the exposed sternal tie and advanced in a posterior direction until the post or stem of the anterior plug is aligned with, and in close proximity to, an anterior opening of the hole through the tissue. The head of the anterior plug may be provided with one or more grooves or cleats in a perimeter thereof, to facilitate securement and tightening of the suture material. The suture material is then used to draw the anterior plug into the anterior opening of the hole through the tissue, and is continually tightened until both the posterior and anterior posts are snugly secured in respective sides of the hole through the tissue. The suture material is secured to the head of the anterior post, such as by tying an appropriate knot or set of knots that can reliably maintain the stability of the posts within the hole in the tissue.

The sternal tie is bent in the direction of the other end of the sternal tie extending from the other side of the tissue to be closed, and once the two ends of the tie are brought together, the tie ends are twisted or otherwise coupled, thereby bringing the two ends of the tissue toward one another, until closure is achieved. The posterior and anterior plugs secured in the tissue serve to buffer the tissue against the sternal tie causing bone cutting, which can detrimentally lead to sternal malunion and bleeding.

In accordance with a first implementation, a tie assembly includes a needle, a tie, a plug, and a tether. The needle has a proximal end and a distal end and the tie extends from the proximal end of the needle. The plug has an axial bore therethrough. The tie is disposed within the bore and the tether tethers the plug to the proximal end of the needle.

In accordance with a second implementation, a method of sternal closure includes inserting a needle through tissue on a first side of an opening to be closed. The needle having a proximal end to which a length of tie and a tether are secured, and by which the tether a plug slidably mounted on the tie is tethered to the needle. The method includes advancing the tether until a head of the plug is brought into registration with a hole through the tissue formed by the needle and severing the needle from the tie and the tether. The method includes threading an additional plug onto an end of the tie exposed by the severing of the needle, securing the tether tightly relative to the additional plug, and advancing the end of the tie toward another end of the tie extending through a second side of the opening to be closed and tightening the wire, thereby closing the tissue.

In further accordance with the foregoing first and/or second implementations, an apparatus and/or method may further include or comprise any one or more of the following:

In an implementation, the plug includes a post having an axial bore therethrough and a head with an opening in communication with the axial bore of the post. The tie is disposed within the bore of the post of the plug, with the head of the plug positioned away from and the post positioned toward the proximal end of the needle along the length of the tie.

In another implementation, the needle is hook-shaped.

In another implementation, the post of the plug is tapered from a relatively narrow diameter farthest from the head to a relatively wider diameter closer to the head.

In another implementation, the tether includes suture material and the head of the plug includes at least one hole therein. One or more of the holes receives the suture material to facilitate the tethering of the plug to the proximal end of the needle.

In another implementation, the at least one hole is formed by a first curved surface and a second curved surface opposite and intersecting the first curved surface.

In another implementation, the needle is removable from the tie and the tether. The tie assembly includes an additional plug threadable onto an exposed end of the tie upon removal of the needle.

In another implementation, a head of the additional plug includes at least one tether-receiving groove therein.

In another implementation, each of the at least one tether-receiving grooves tapers inwardly from a perimeter of the head toward an axis of the additional plug.

In another implementation, each of the tether-receiving grooves further tapers vertically from a bottom toward a top of the head of the additional plug.

In another implementation, each of the tether-receiving grooves includes tapered surfaces that extend inward from a perimeter of the head toward an entrance of a tear-drop shaped opening of the corresponding tether-receiving groove.

In another implementation, the at least one tether-receiving groove includes a pair of tether-receiving grooves.

In another implementation, the tether-receiving grooves are positioned approximately 180° from one another.

In another implementation, the tether-receiving groove is formed by a cleat.

In another implementation, the cleat includes a plurality of inwardly extending teeth.

In another implementation, the additional plug has an axial bore and the cleat has an opening adjacent the axial bore.

In another implementation, the additional plug has an axial bore and the cleat has a groove adjacent to and radially extending from the axial bore.

In another implementation, the additional plug includes a ratchet having a pawl and the tether includes a plurality grooves that are engagable by the pawl.

In another implementation, the ratchet includes a U-shaped wall in which the pawl is movable.

In another implementation, the additional plug includes an opening to allow the tether to pass through the additional plug and through the ratchet.

In another implementation, the tether is integral with the plug.

In another implementation, the pawl includes a plurality of teeth that are engagable with corresponding grooves of the tether.

In another implementation, the tether is coupled to the plug.

In another implementation, the additional plug includes an opening and the tether includes a plurality of barbs spaced along the tether and engagable against a surface of the additional plug surrounding the opening.

In another implementation, the additional plug includes a surgical clip to secure the tether relative thereto.

In another implementation, the tie assembly also includes a base having a plurality of spaced apart projections. The tie assembly also includes a plurality of additional plugs each having an axial bore through which a corresponding projection extends.

In another implementation, the tie assembly includes adhesive on a surface of the base opposite the projections.

In another implementation, the tie assembly includes a release label disposed over the adhesive.

In another implementation, the needle is a first needle and the plug is a first plug. The tie assembly also includes a second needle having a proximal end and a distal end. The second needle is disposed at an opposite end of the tie from the first needle, with the tie extending from the proximal end of the second needle, and a second plug tethered by an additional tether to the proximal end of the second needle.

In another implementation, the second plug has a post with an axial bore therethrough and a head with an opening in communication with the axial bore of the post. The tie is disposed within the bore of the post of the second plug, with the head of the second plug positioned away from and the post of the second plug positioned toward the proximal end of the second needle along the length of the tie.

In another implementation, the head of the second plug includes at least one hole therein, one or more of the at least one hole of the head of the second plug receives the tether, to facilitate the tethering of the second plug to the proximal end of the second needle.

In another implementation, the first and second plugs are posterior plugs and the first and second needles are severable from the tie and the tether. The tie assembly includes a pair of anterior plugs, each of which is threadable onto an exposed end of the tie upon removal of a respective one of the first and second needles.

In another implementation, a head of each of the anterior plugs includes at least one tether-receiving groove therein.

In another implementation, each of the tether-receiving grooves tapers inwardly from a perimeter of the head of the associated anterior plug toward an axis of the associated anterior plug.

In another implementation, each of the tether-receiving grooves further tapers vertically from a bottom toward a top of the head of the associated anterior plug.

In another implementation, the tether includes suture material.

In another implementation, in inserting the needle, the needle is a first needle, and the method further includes inserting a second needle through tissue on the second side of the opening to be closed. The second needle having a proximal end to which a second end of the length of tie and an additional tether are secured, and by which the additional tether a second plug slidably mounted on the tie is tethered to the second needle. The method includes advancing the additional tether until a head of the second plug is brought into registration with a hole through the tissue formed by the second needle and severing the second needle from the tie and the additional tether. The method includes threading yet an additional plug onto the end of the tie exposed by the severing of the second needle and securing the additional tether tightly relative to the yet additional plug.

In another implementation, one or more of the plugs further includes a post, and the method includes inserting the post into one of the holes formed in the tissue.

BRIEF DESCRIPTION OF THE SEVERAL
VIEWS OF THE DRAWING

FIG. 18 is a flow chart explanation of the sequence of steps in a preferred technique or manner of use of the sternal tie assembly of the present disclosure;

FIG. 30A is a cross-sectional view of the tie assembly of FIG. 28 used to close two ends of tissue together;

FIG. 30B is a cross-sectional view of another tie assembly 470 used close two ends of tissue T together;

DETAILED DESCRIPTION OF THE PREFERRED EMBODIMENTS

The present disclosure relates generally to improved medical devices and techniques for performing tie cerclage closure of the sternum, and more particularly, to a sternal tie assembly having at least one integral needle, a sternal tie extending from a proximal end of the needle, suture material secured to the needle, and a plug tethered to the needle by the suture material, such that after passage of the needle through sternum, manubrium, ribs, costal cartilage, intercostal muscle, or other tissue, the needle and suture material can be pulled to advance a hollow post or stem of the posterior plug into or adjacent to a posterior entry of the formed needle hole, the hollow post or stem permitting the posterior plug to receive and ride along the sternal tie. Further aspects of the disclosure include a second, anterior plug having a hollow post or stem that can be advanced into or adjacent to an anterior exit of the formed needle hole. The second, anterior plug may be provided with a plug head with one or more cleats or grooves in a perimeter thereof to facilitate tightening of the suture material so as to draw the posterior and anterior plugs toward one another and tightly secure them in place in the needle hole through the sternum, manubrium, rib, costal cartilage, intercostal muscle, or other tissue. Alternately, a plug may be provided with no (or only a very short) post or stem, for applications in which it is not necessary to introduce the plug into a channel or hole formed by the needle, but merely provide the plug for tamponade. Additional details and features are provided in the figures and described below.

Figure 1:
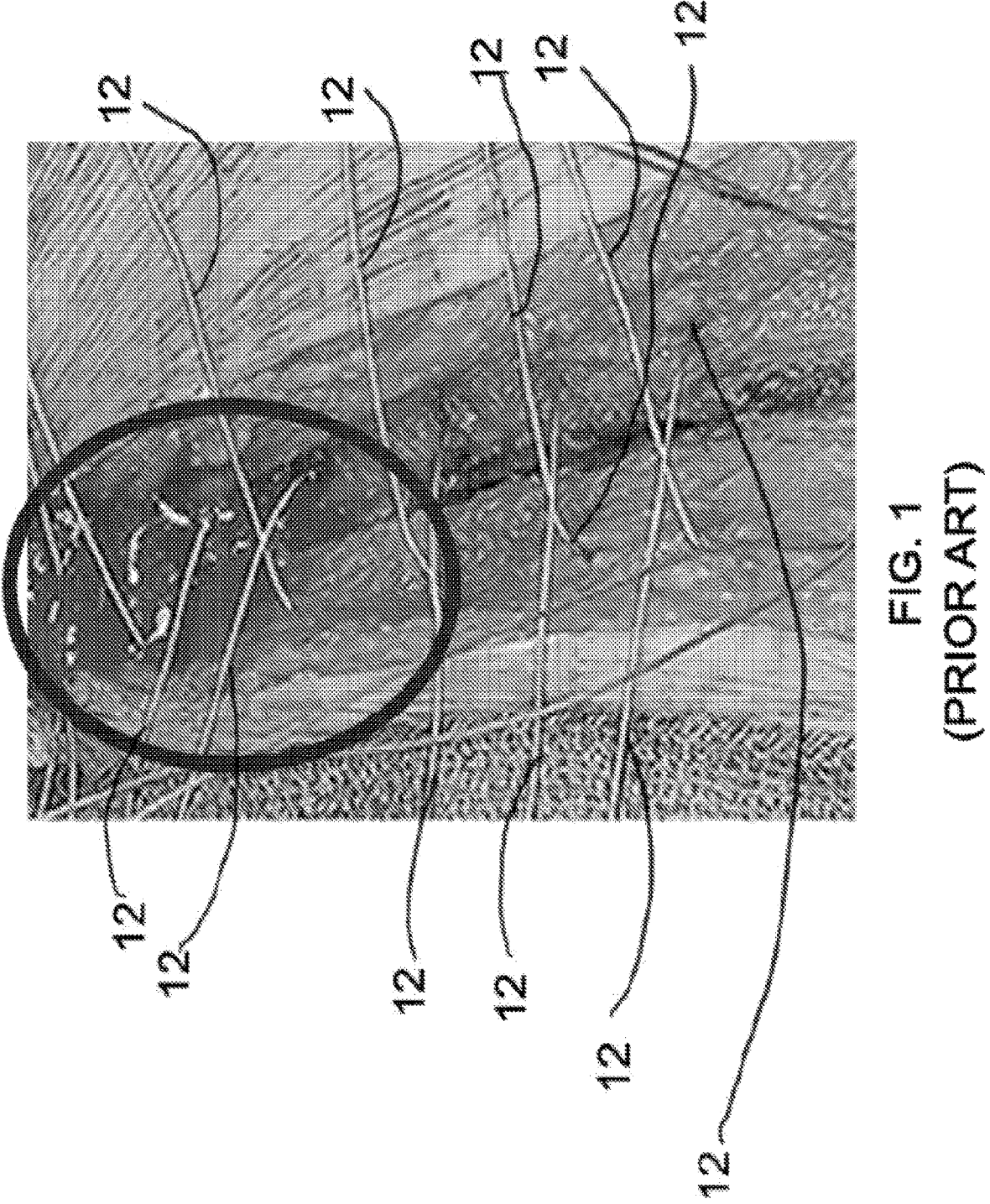
FIG. 1 is a perspective view of a wire closure following a sternotomy using a plurality of conventional (prior art) sternal wires.

With reference to FIG. 1, a wire cerclage closure using a conventional set of sternal wires is illustrated. In a typical procedure, a set of approximately seven J-shaped (i.e., hook-shaped) needles, each integral with a respective sternal wire 12 extending from a proximal end thereof (illustrated in FIG. 2), is inserted through sternum, manubrium, rib, rib cartilage, intercostal muscle, or other tissue. Each of the sternal wires 12 is then crossed with a sternal wire 12 of a needle inserted through the sternum, manubrium, rib, rib cartilage, intercostal muscle, or other tissue on the other side of the sternal separation, then the sternal wires 12 are twisted until closure is achieved. While efforts have been made to develop grommets, cylinders, or other inserts to provide such isolation, as discussed in the BACKGROUND section of this disclosure, these efforts have heretofore not provided a satisfactory solution to the problems of delivery of such devices to the holes in the tissue formed by the needle, and securement of the devices to the tissue.

Figures 2, 3:
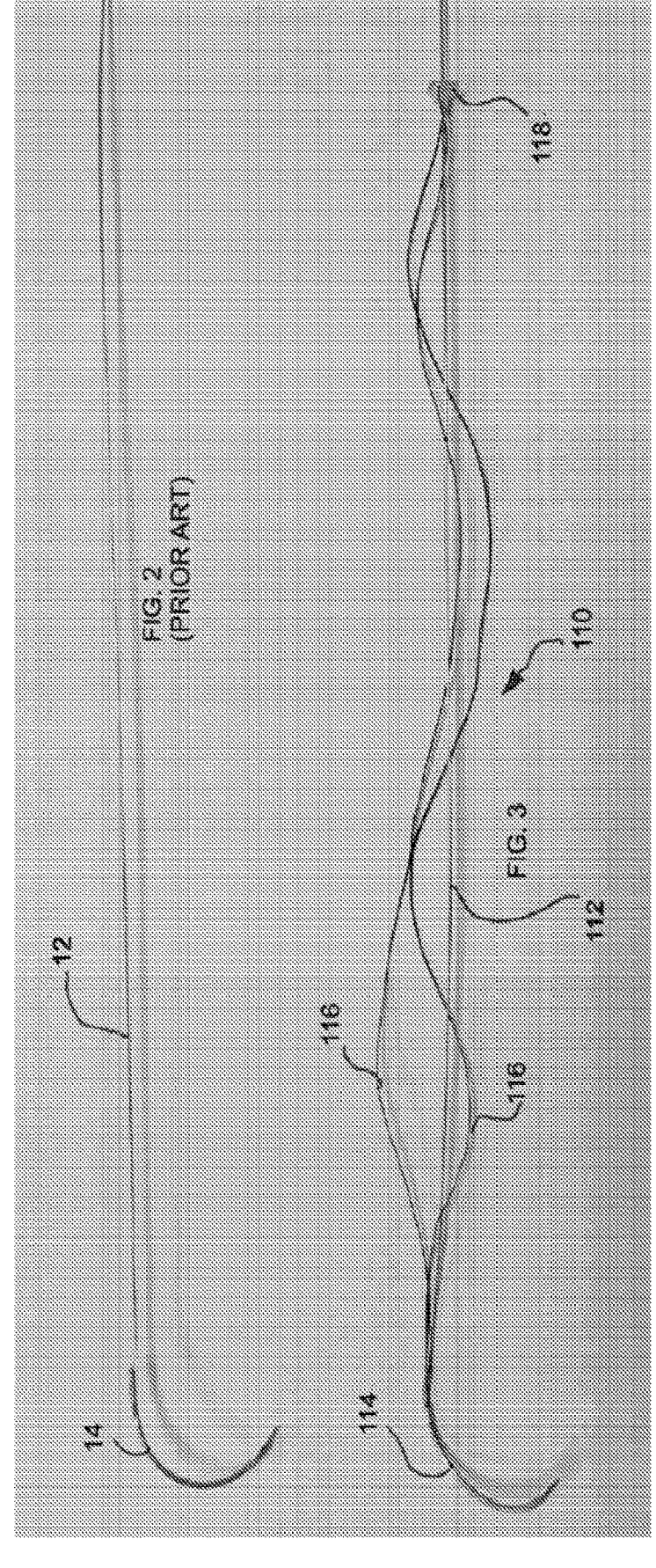
FIG. 2 is a plan view of a conventional needle having a sternal wire integral with, and extending from, a proximal end thereof.
FIG. 3 is a plan view of a needle of the present disclosure having a sternal tie integral with, and extending from, a proximal end thereof, and further provided with a posterior plug slidably received on the sternal tie, the posterior plug tethered to the proximal end of the needle by suture material.
Figure 4:
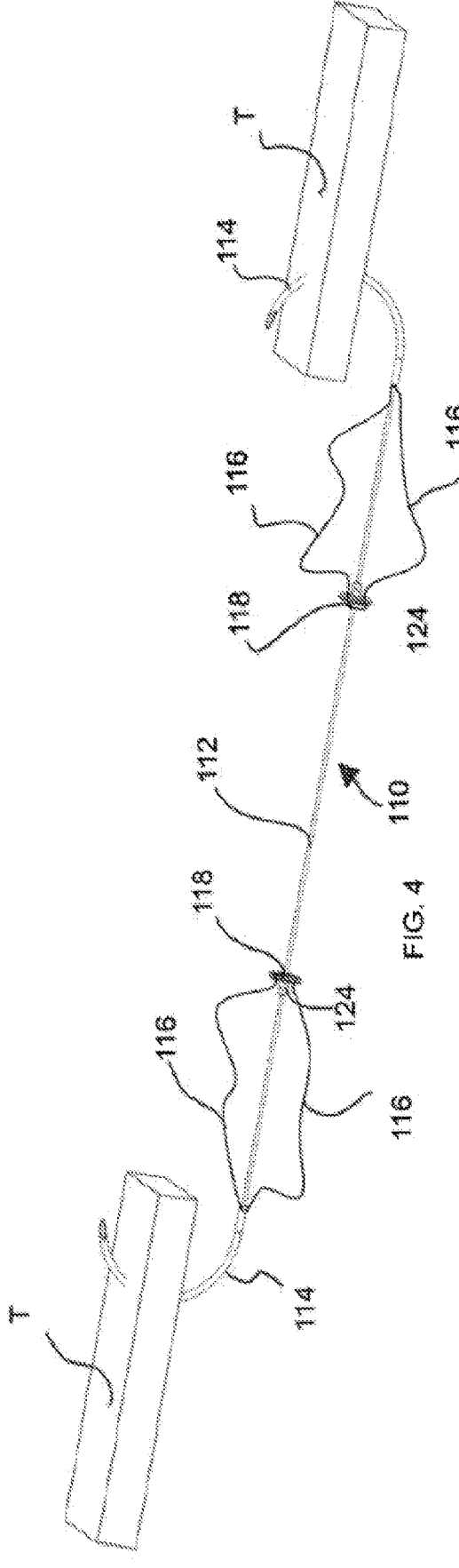
FIG. 4 is an anterior perspective view of a sternal tie assembly of the present disclosure, including a pair of needles, each of which engaged with a respective end of separated tissue to be closed, the tissue, for example sternum, manubrium, rib, rib cartilage, or intercostal muscle, illustrated schematically for ease of illustration.

The sternal tie assembly 110 of the present disclosure resolves these and other shortcomings of conventional needle/sternal wire constructs, as illustrated in FIGS. 3 and 4, by providing a posterior plug 118 (also referred to herein simply as a plug 118) that is tethered by a tether 116 (which includes at least one length of line and/or suture line) to a proximal end of a needle 114. The tether 116 may be suture material or the tether 404 having ribs 412 and grooves 414 (see, FIG. 26) as further disclosed below. The posterior plug 118 includes a hollow post or stem 124, and the bore through the post or stem 124 extends through the head or crown of the plug 118, such that the plug 118 can axially receive, and slide along, a sternal tie 112. As set forth herein, the term "tie" may include a wire, a string, a cord, or anything used for fastening and may include, for example, stainless steel, another metal, and/or plastic, such as example, polyethere-therketone (PEEK). The tie 112 may have any cross-section including a circular cross-section, an oblong cross-section, and/or a rectangular cross-section. The tie 112 may also include a fastener to secure ends of the tie together. The fastener may include a ratchet and pawl (e.g., similar to a cable tie), a surgical clip, a crimp, etc. Alternatively, ends of the tie 112 may be secured by twisting the ends together or by fusing the ends together. Alternatively, the posterior plug 118 may be provided with no stem, or only a very short (stub-like) stem or post, in applications were the posterior plug 118 need not enter the hole or channel formed by the needle 114, but can still serve a tamponade function. Both the sternal tie 112 and the suture material 116 are secured to, or integral with, a proximal end of the needle 114.

Preferably, a pair of opposing needles 114 are provided at opposite ends of a length of sternal tie 112. Each of the needles 114 is preferably J-shaped (i.e., hook-shaped) to facilitate insertion, posteriorly-to-anteriorly, through sternum, manubrium, rib, rib cartilage, intercostal muscle, or other tissue.

Figure 11:
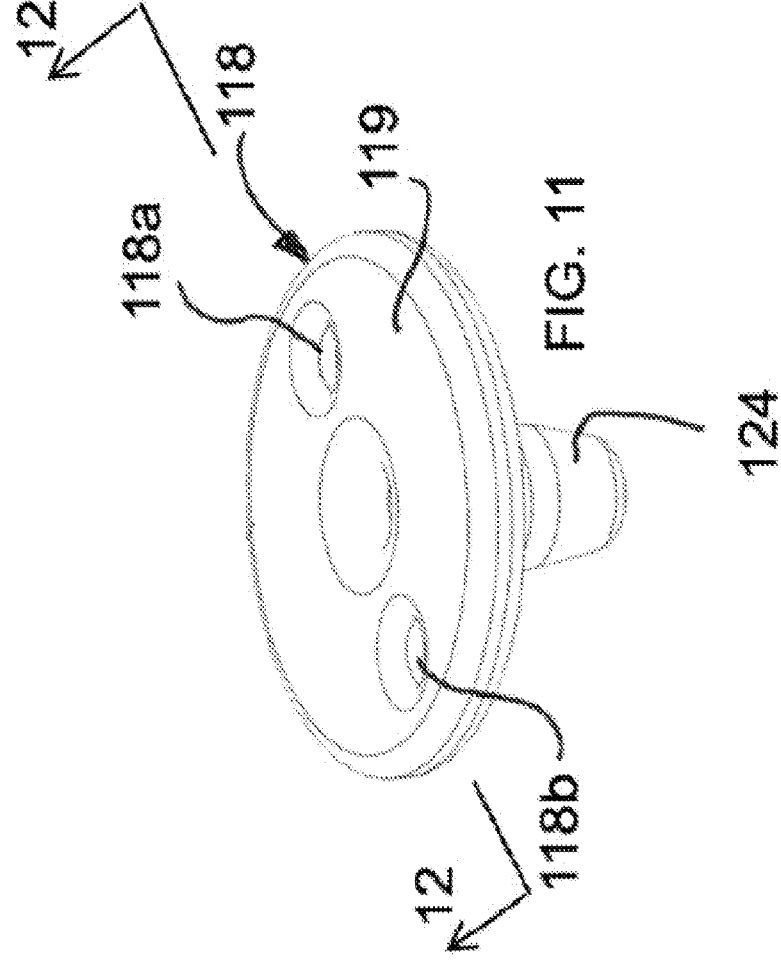
FIG. 11 is a top perspective view of a posterior plug of the sternal tie assembly of the present disclosure.
Figure 12:
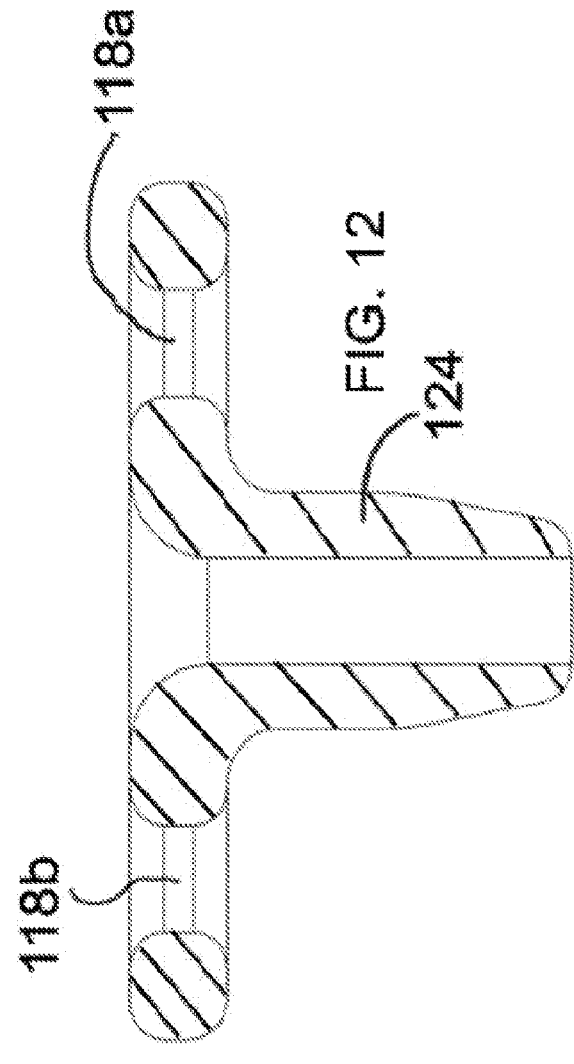
FIG. 12 is a cross-section of the posterior plug taken along lines 12-12 of FIG. 11.

The hollow post or stem 124 of each of the posterior plugs 118 faces the proximal end of the respective needle 114 to which it is tethered by the suture material 116. With reference to FIGS. 11 and 12, the head or crown 119 of the plug 118 includes one or more, preferably two, suture holes 118a, 118b, to which the suture material 116 is secured. Alternatively, the suture material 116 may be affixed to the plug 118 by other means, such as adhesive, or may have a portion that is embedded within the plug or secured between two layers of a stacked head, similar to a washer and a head of a bolt. The outer surface of the post or stem 124 is preferably tapered inwardly, as illustrated in FIG. 12, to facilitate insertion of the plug 118 in the hole through the tissue T formed by the needle 114.

Figures 5, 6:
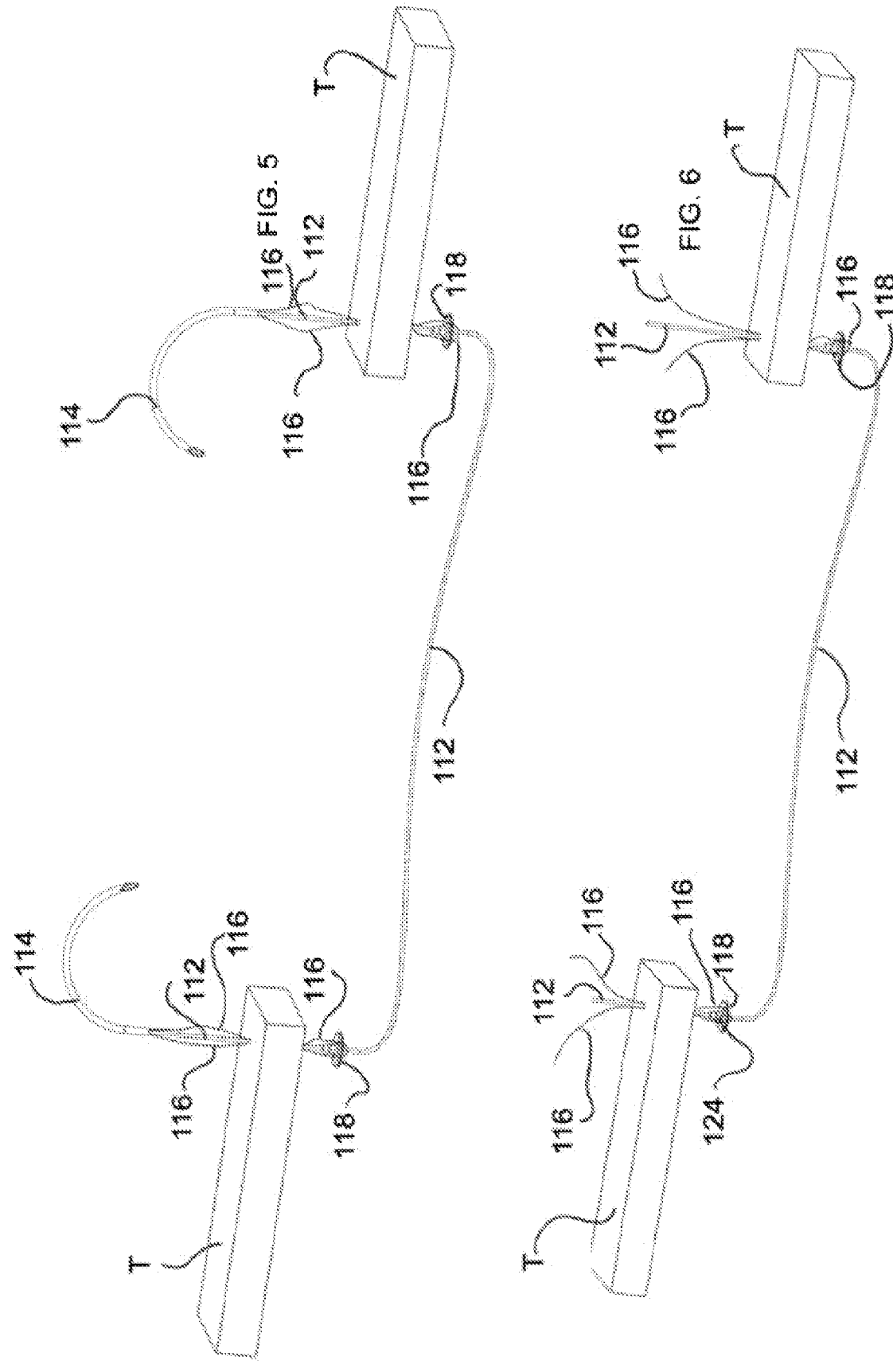
FIG. 5 is an anterior perspective view of the sternal tie assembly of the present disclosure, illustrating a condition immediately after the needles are advanced through the respective ends of the separated tissue, with a length of sternal tie and suture material extending through the holes formed by the needles through the tissue.
FIG. 6 is an anterior perspective view of the sternal tie assembly of the present disclosure, illustrating a condition after the needles are severed from the sternal tie and suture material.

As illustrated in FIGS. 4-9, a method of use of the sternal tie assembly 110 of the present disclosure involves first, inserting the distal end of each of the needles 114 of the assembly 110 through one of the two exposed ends of the sternum, manubrium, rib, rib cartilage, intercostal muscle, or other tissue T that are desired to be closed toward one another. As illustrated in FIG. 5, the needles 114 are then advanced through the holes formed through the tissue T, and once the needles 114 are pulled out an anterior side of the tissue T, the trailing sternal tie 112 and the suture material 116 secured to or integral with the proximal end of the associated needle 114 necessarily follow. Advantageously, continued advancement of the needles 114 and the suture material 116 brings the tethered plugs 118 into alignment with the one of the holes through the tissue T just formed by the needles 114, which holes are maintained by the sternal tie 112.

Figures 7, 8:
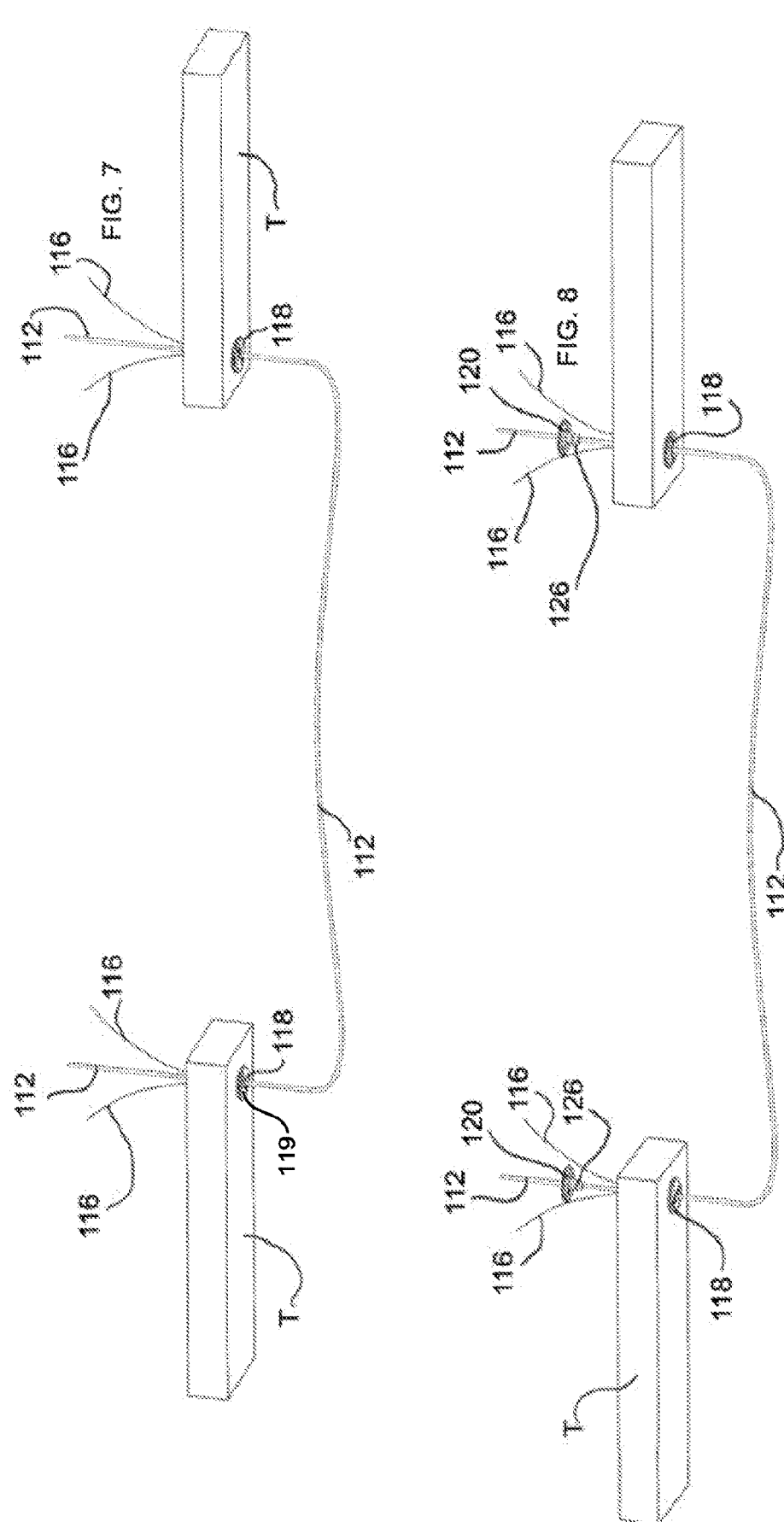
FIG. 7 is a posterior perspective view of the sternal tie assembly of the present disclosure, illustrating a condition after the suture material has been utilized to pull the posterior plugs into respective posterior openings of the holes through the tissue formed by the severed needles.
FIG. 8 is a posterior perspective view of the sternal tie assembly of the present disclosure, illustrating anterior plugs threaded along the exposed ends of the sternal tie.

The needles 114 are then severed from the sternal tie 112 and from the suture material 116, as illustrated in FIG. 6. By pulling the suture material 116 anteriorly, the tapered post or stem 124 of each of the posterior plugs 118 enters the posterior side of the associated hole through the tissue T, and the surgeon may continue pulling on the suture material 116 until resistance is encountered, likely indicating the head or crown 119 of the plug 118 has made contact with the posterior side of the tissue T, as illustrated in FIG. 7. The surgeon may also confirm that the posterior plug 118 is secure and in place by reaching one or more fingers around the sternal edge and palpating the location and positioning of the head or crown 121 of the plug 118 relative to the tissue T. It is recognized the surgeon may elect to directly advance the stem or post 124 of the posterior plug 118 through the hole or channel formed in the tissue T by pushing the plug 118 into place, rather than by pulling on the suture material 116. Alternatively, the plug 118 may seat against an entrance formed by the needle hole but the plug 118 may not enter or substantially enter the needle hole.

Figure 13:
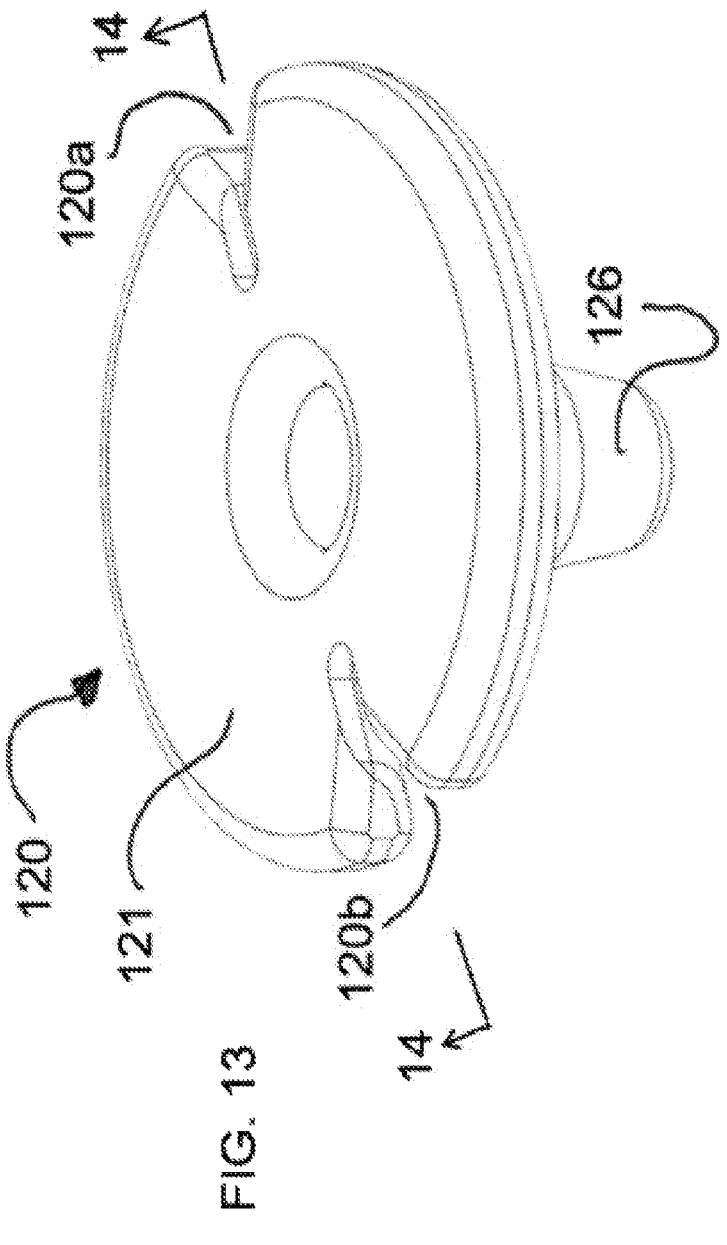
FIG. 13 is a top perspective view of an anterior plug for use in combination with the rest of the sternal tie assembly of the present disclosure.
Figure 14:
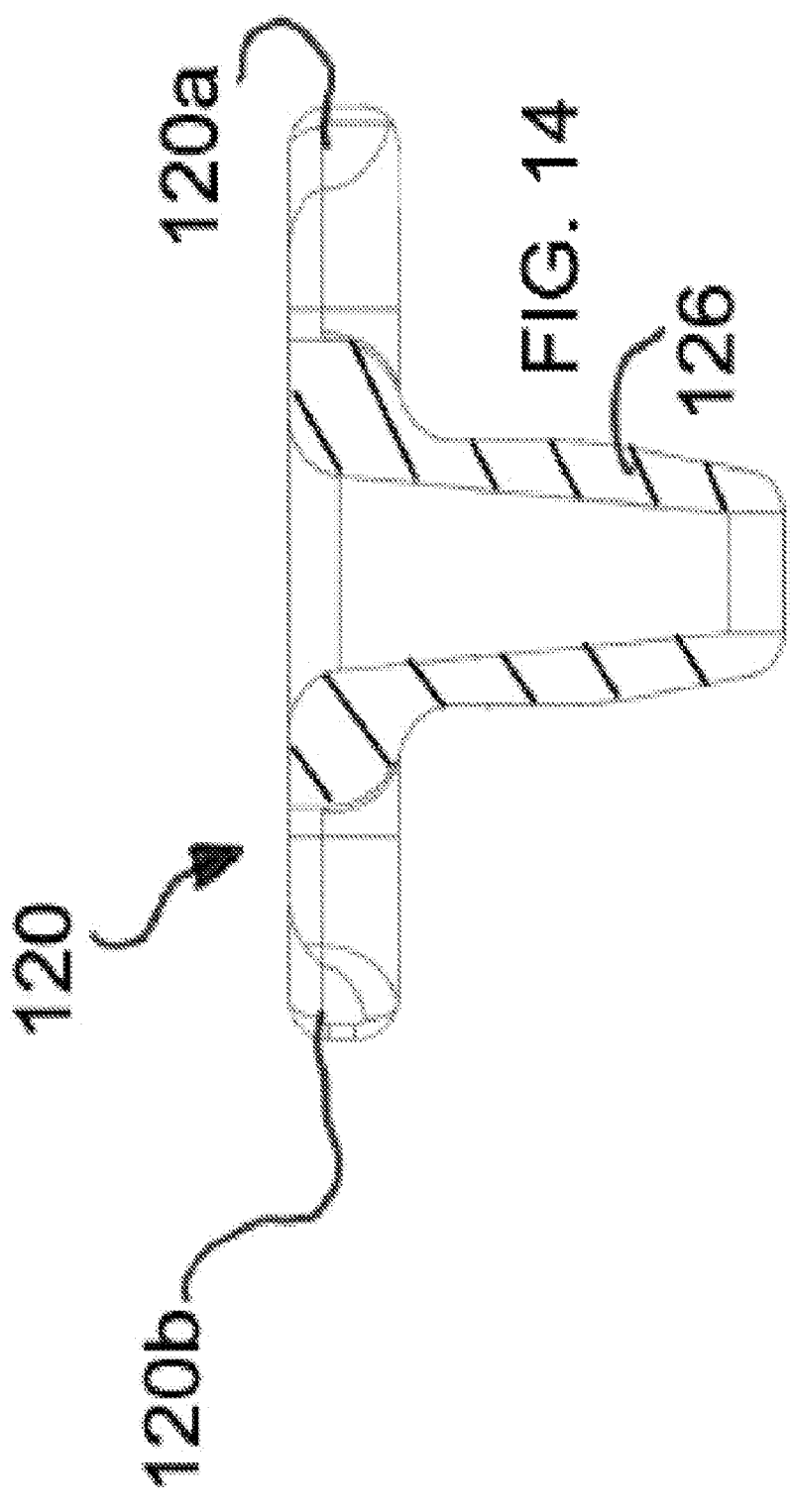
FIG. 14 is a cross-section of the anterior plug taken along lines 14-14 of FIG. 13.
Figure 15:
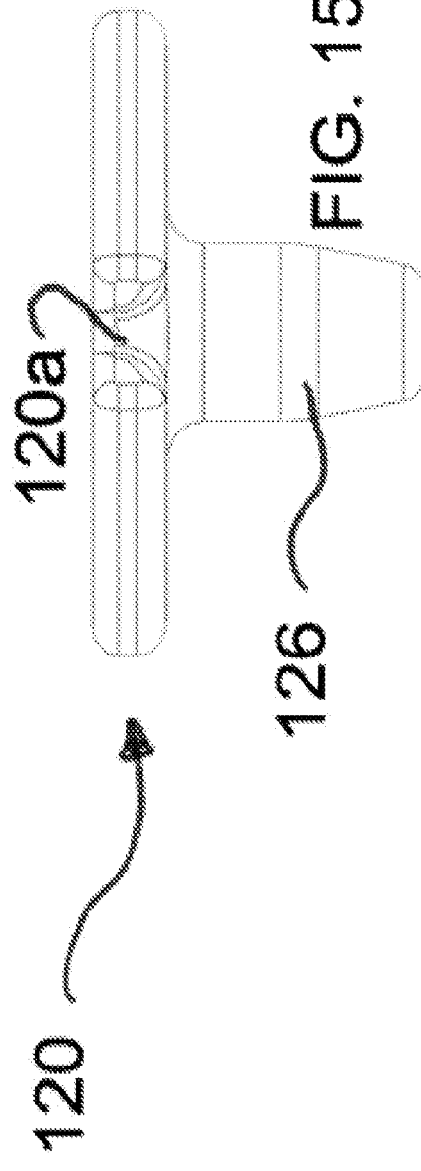
FIG. 15 is a front elevation view of the anterior plug of FIG. 13, illustrating a dual-tapered cleat or groove in a head of the anterior plug to facilitate securement of suture material thereto.
Figure 16:
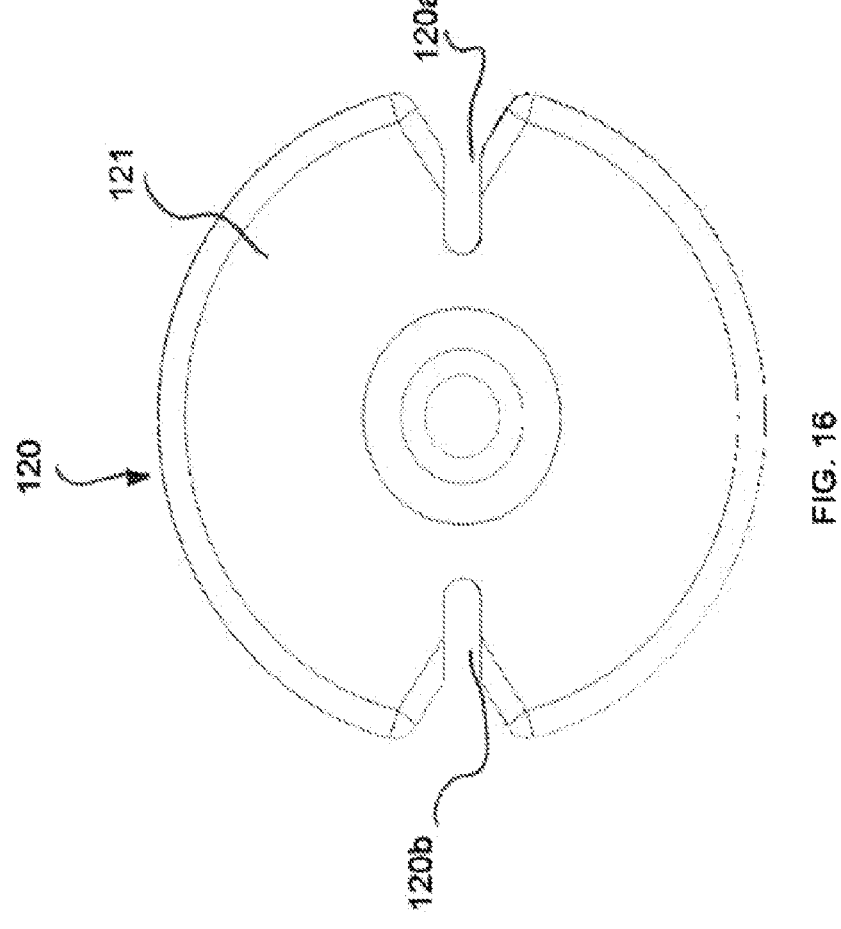
FIG. 16 is a top plan view of the anterior plug of FIG. 13.
Figure 17:
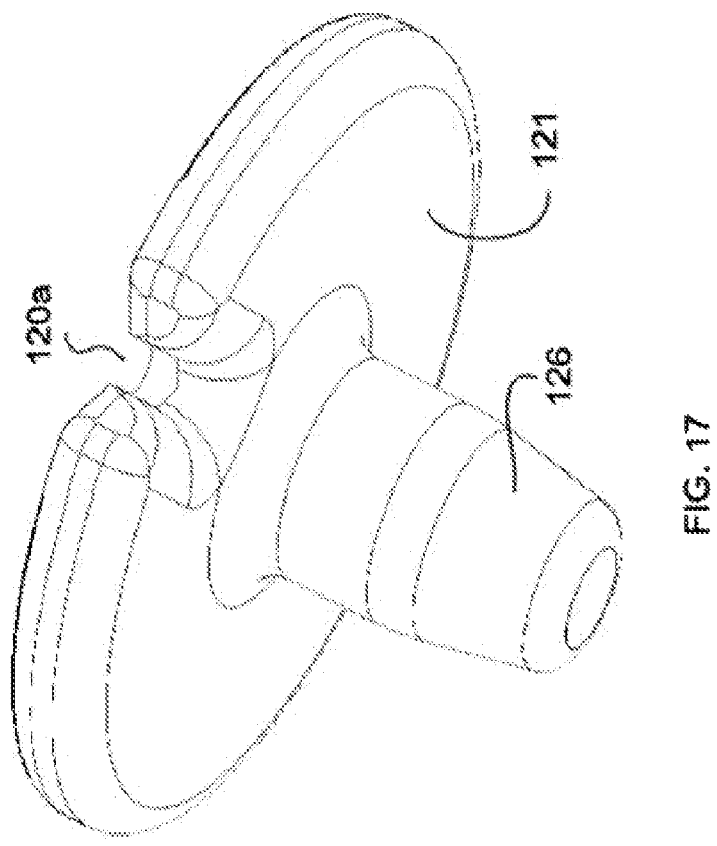
FIG. 17 is a bottom perspective view of the anterior plug of FIG. 13.

Next, an anterior plug 120 is threaded onto each exposed end of the sternal tie 112, as illustrated in FIG. 8, with a stem or post of the anterior plug 120 facing the anterior end of the hole formed through the tissue T. To facilitate securement of the suture material 116 to the anterior plug 120, instead of suture holes 118a, 118b, like in the head or crown 119 of the posterior plug 118, the head or crown 121 of each of the anterior plugs 120 is provided with a pair of radially inwardly-directed grooves or cleats 120a, 120b, as seen in FIGS. 13-14. The grooves 120a, 120b may be referred to as suture-receiving grooves or tether receiving grooves. The grooves or cleats 120a, 120b are preferably tapered from a widest point at a perimeter of the head or crown 121, down to a channel having a constant or substantially-constant width toward an axis of the plug 120. As best illustrated in FIG. 17, the grooves or cleats 120a, 120b preferably taper not only inwardly, but also vertically, from a bottom of the head or crown 121 toward the top of the head or crown 121. This dual-dimension taper is believed to best facilitate ease of insertion and retention of the exposed suture material 116. The grooves or cleats 120a, 120b serve as a continuous cleat or synching mechanism, permitting the suture material 116 to tighten, but not loosen, as the plugs 118, 120 are secured within the hole or channel formed through the tissue T by the needle 114.

Like the post or stem 124 of the posterior plug 118, the outer surface of the post or stem 126 is preferably tapered inwardly, as illustrated in FIG. 14, to facilitate insertion of the anterior plug 120 in the hole through the tissue T formed by the needle 114. Additionally, the bore or channel within the plug 118, extending through the post or stem 126 and through the head or crown 121, can also be tapered, from a relatively wide diameter at a proximal end of the head 121, inwardly to a relatively narrow diameter at a distal end of the post 126, opposite from the head 121. The external taper of the post 126 facilitates insertion of the plug 120 into the hole in the tissue T formed by the needle 114, and the internal taper of the channel within the plug 118 allows the plug 118 to more easily slide along the sternal tie 112. Advantageously, the internal and external tapers aid in manufacture of the plugs if they are injection molded, as tapered surfaces are more easily ejected from mold cavities of injection molding systems.

Figure 9:
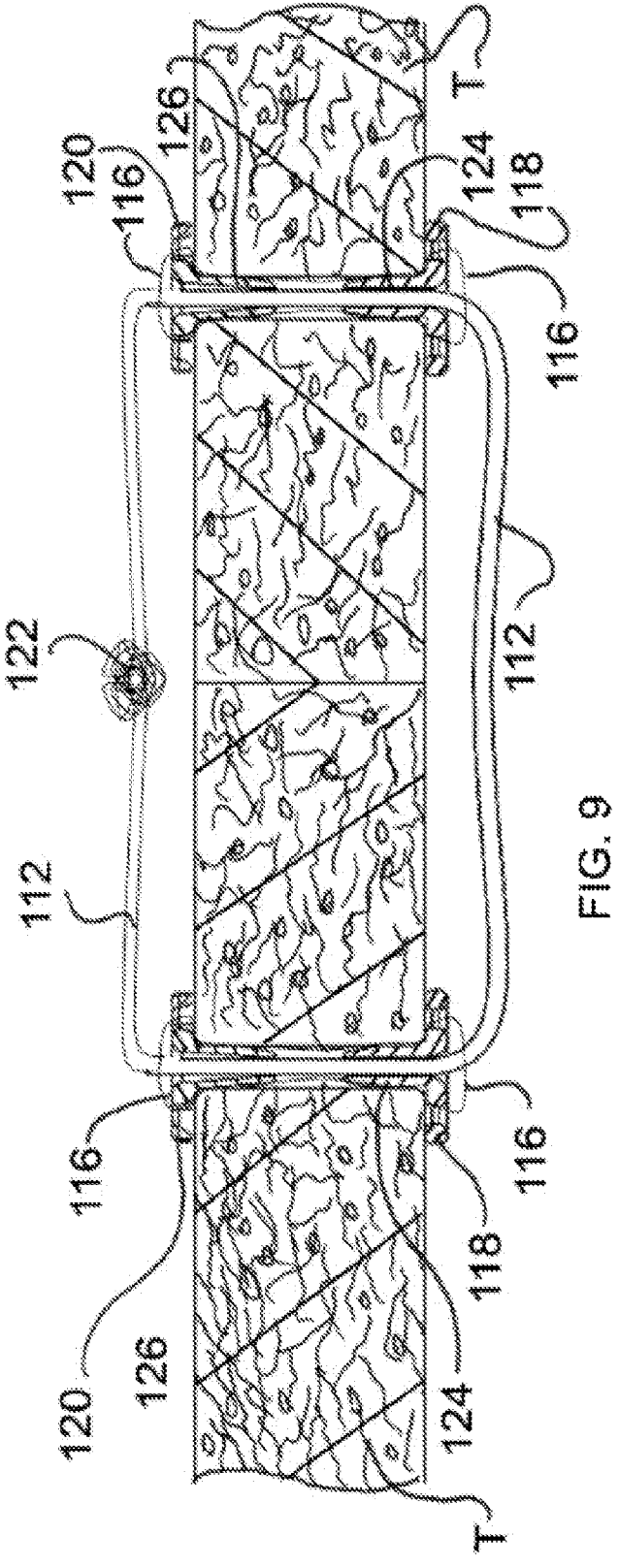
FIG. 9 is a cross-sectional view of the sternal tie assembly of the present disclosure in a final condition, with the posterior and anterior plugs secured in place by the suture material, and the sternal tie tightened to achieve tissue closure.
Figure 10:
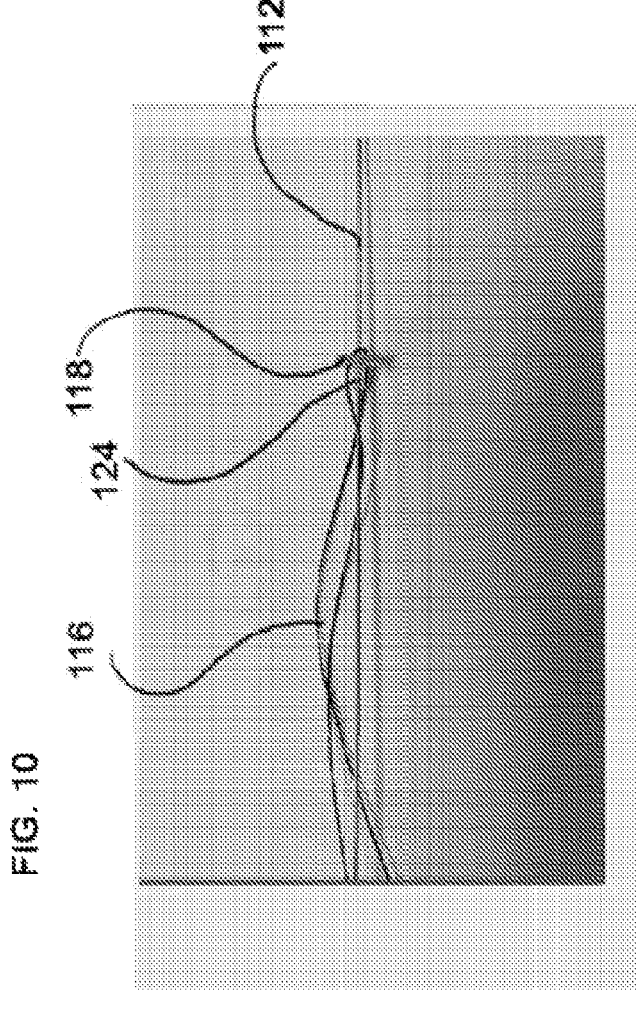
FIG. 10 is a plan view of a posterior plug of the sternal tie assembly of the present disclosure slidably received on a length of sternal tie, and suture material tethering the posterior plug to a proximal end of a needle (not shown) of the sternal tie assembly.

Finally, as illustrated in cross-section in FIG. 9, suture material 116 is used to secure the anterior plugs 120 to the tissue T, and then the exposed ends of the sternal tie 112 are brought together and twisted, as indicated by reference number 122, thereby promoting closure of the two ends of the tissue T. In this implementation, the ends of the suture 116 may be tied together, pulling both the posterior and anterior plugs 118, 120 together and substantially ensuring that the plugs 118, 120 do not dislodge or migrate over time.

In securing the anterior plugs 120 to the tissue T, there are two suture knot options that will work well for this application, both of which are intended to maintain tension in the suture as the knot is tied. 1) A surgeon's knot (this is a reef knot with the application of an extra twist to yield a double overhand knot), followed by 2-3 additional reef knots, tied in alternating directions. Alternatively, 2) A slip knot (this is two reef knots, tied in the same direction so that the knot can be slipped down onto the structure around which the suture is placed), followed by 2-3 additional reef knots, tied in alternating directions.

The entirety of the sternal tie assembly 110 of the present disclosure, or one or more of the sternal tie 112, the suture material 116, and the posterior plugs 118 and anterior plugs 120 thereof, may be made of a biocompatible material intended for permanent indwell. Alternatively, one or more of these components of the sternal wire assembly 110 may be made of a bioabsorbable material, dissolving in vivo over time. Alternatively, one or more of these components may be made of a hemostatic material which facilitates and expedites local blood clotting.

Figure 19:
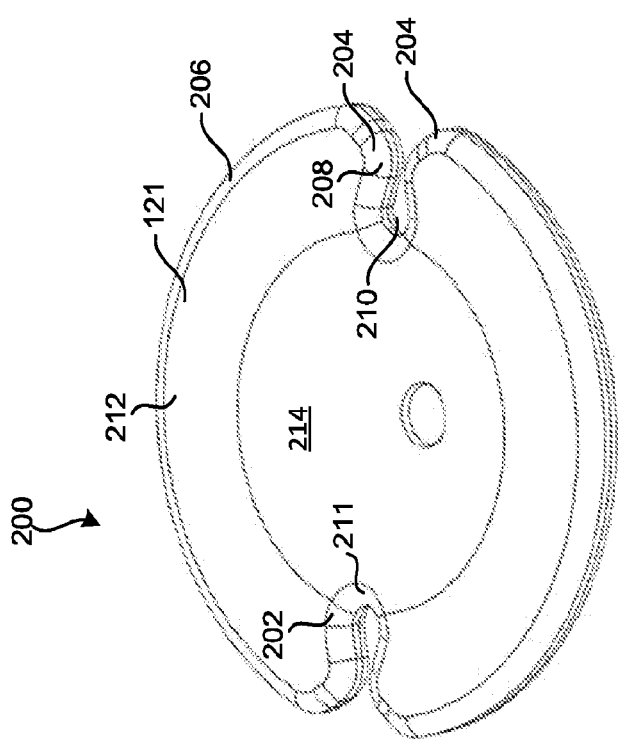
FIG. 19 is an isometric view of another implementation of a plug that can be used with the sternal tie assembly of FIG. 3.

FIG. 19 is an isometric view of another implementation of a plug 200 that can be used with the sternal tie assembly 110 of FIG. 3. The plug 200 is similar to the plug 120 of FIG. 13. However, in contrast, the plug 200 of FIG. 19 includes alternative tether-receiving grooves 202. In the implementation shown, the grooves 202 include tapered surfaces 204 that extend inward from a perimeter 206 of the head 121 of the plug 200 toward an entrance 208 of a tear-drop shaped opening 210 of the corresponding groove 202. The entrance 208 is a narrower region of the groove 202 that allows the suture material 116 to pass therethrough before being received within the tear-drop shaped opening 210. The grooves 202 are shown as a pair of grooves 202 that are positioned approximately 180° degrees relative to one another. The grooves 202 are also mirror images of one another and the plug 200 includes a surface 211 that tapers vertically upward from a top surface 212 of the head 121 toward a bottom of the head 121. Opposite the surface 211, the plug may include a surface that tapers vertically downward from the bottom of the head 121 toward the top 214 of the plug 200.

Figures 20, 21:
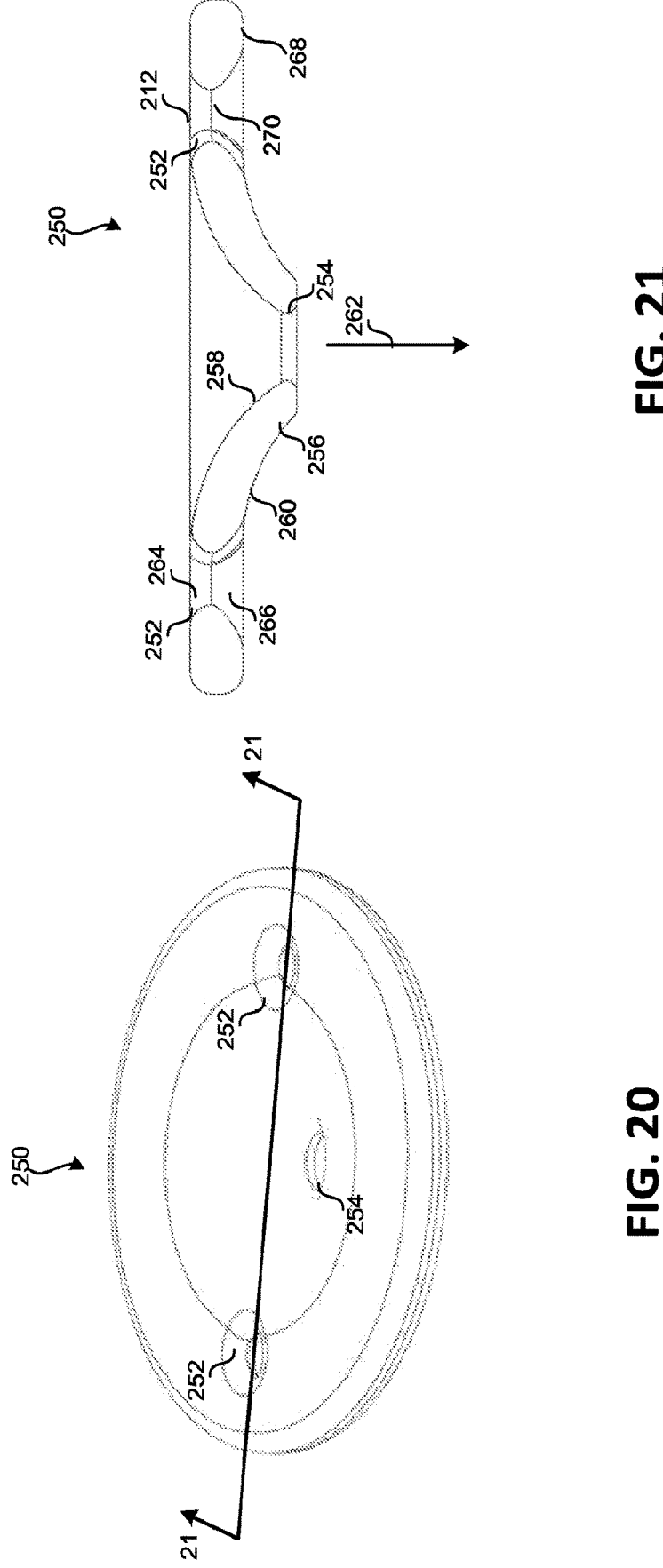
FIG. 20 is an isometric view of another implementation of a plug that can be used with the sternal tie assembly of FIG. 3.
FIG. 21 is a cross-sectional view of the plug of FIG. 20 taken along lines 21-21.

FIG. 20 is an isometric view of another implementation of a plug 250 that can be used with the sternal tie assembly 110 of FIG. 3. In the implementation shown, the plug 250 includes a pair of holes 252 that receive the tether/suture material 116 and an axial bore 254 that receives the tie 112.

FIG. 21 is a cross-sectional view of the plug 250 of FIG. 20 taken along lines 21-21. In the implementation shown, the plug 250 includes a hollow post or stem 256 that is formed by an inner curved surface 258 and an outer curved surface 260. The curved surfaces 258, 260 taper toward one another in a direction generally indicated by arrow 262. The holes 252 are shown being formed from a first curved surface 264 that curves outwardly toward the top 212 of the plug 250 and a second curved surface 266 that curves outwardly toward a bottom surface 268 of the plug 250. The curved surfaces 264, 266 intersect toward at a central area 270 of the hole 252.

The stem 256 of the plug 250 is designed to focus compressive force onto the entrance of the needle hole formed by the needle 114 without or without significantly going into the needle hole itself. Designing the stem 256 to seat against the entrance of the needle hole allows the plug 250 to more easily translate over the sternal tie/tether 116 because the axial bore 254 of the plug 250 has a less narrow channel as would otherwise be provided if the stem 256 were longer. Designing the stem 256 to seat against the entrance of the needle hole may also reduce the likelihood of the plug 250 fracturing because the length of the stem 256 is reduced. Moreover, it has been found that as the stems 256 settle relative to the needle hole and/or the entrance of the needle hole, the stiffness and/or strength of the coupling formed by the associated tie assembly may increase overtime. As such, the tie assemblies in accordance with the teachings of this disclosure have a lesser likelihood to fail during fatigue testing.

Figure 22:
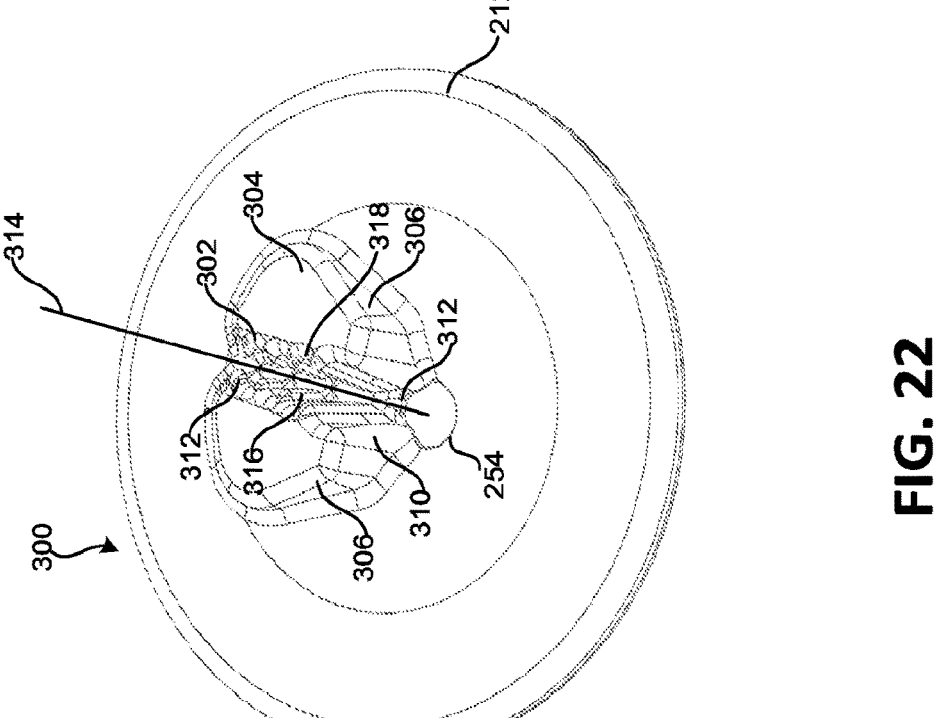
FIG. 22 is an isometric top view of another implementation of a plug that can be used with the sternal tie assembly of FIG. 3.

FIG. 22 is an isometric top view of another implementation of a plug 300 that can be used with the sternal tie assembly 110 of FIG. 3. The plug 300 of FIG. 22 includes a tether-receiving groove 302 that is formed by a cleat 304. The cleat 304 can be sized to receive, for example, a suture/tether 116 having a size 0 to a 3-0, although other sizes are contemplated.

The cleat 304 includes two protrusions 306 that extend from the top 212 and form the groove 302 therebetween. The groove 302 has an opening 310 positioned to allow the tether 116 to be received within the groove 302. The opening 310 is at least partially formed by a curved surface 312 that deters a kink or 90° bend from being placed in the tether 116.

Still referring to the protrusions 306 of the cleat 304, in the implementation shown, the protrusions 306 are symmetric about a radial axis 314 and each have an inward facing surface 316 that form the groove 302. The inward facing surfaces 316 have inwardly extending teeth 318 that are used to secure the tether 116 within the cleat 304. The teeth 318 are also shown being symmetric across the radial axis 314. However, the teeth 318 may be differently positioned and/or shaped or the teeth 318 may be omitted. To secure the tether 116 within the cleat 304, the anterior plug 300 may be pushed down and the tether 116 can be placed in the cleat 304, holding the anterior and posterior plugs 250, 300 in place.

Figure 23:
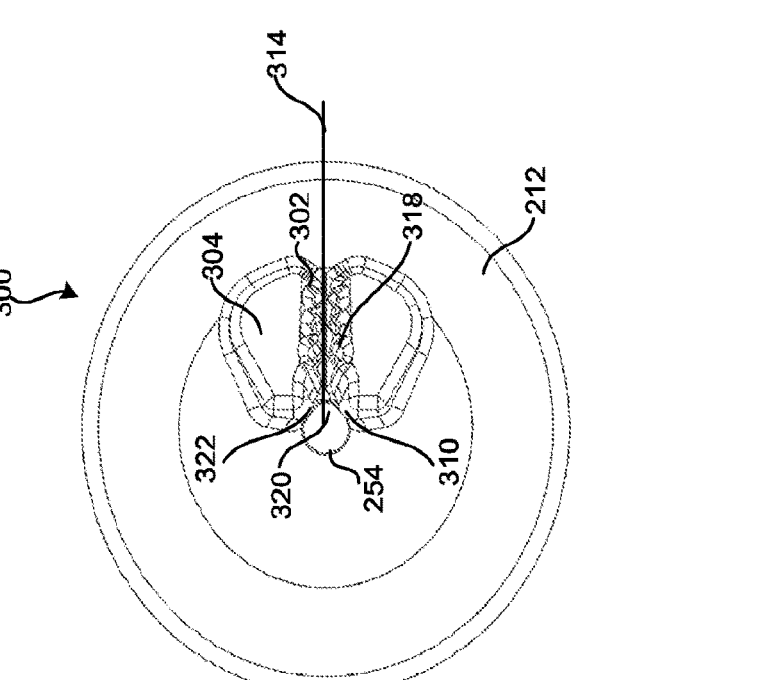
FIG. 23 is a top view of the plug of FIG. 22.
Figure 24:
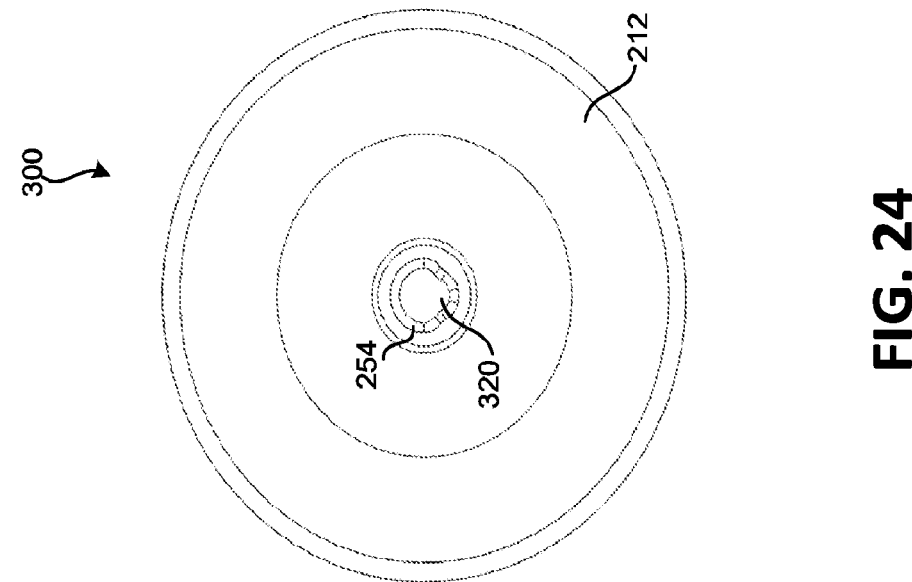
FIG. 24 is a bottom view of the plug of FIG. 22.

FIG. 23 is a top view of the plug 300 of FIG. 22 and FIG. 24 is a bottom view of the plug 300 of FIG. 22. As shown in both FIG. 23 and with reference to FIG. 24, the axial bore 254 of the plug 300 includes a notch 320 positioned beneath the opening 310 of the groove 302 that may encourage the tether 116 to enter and/or remain in the groove 302. As also shown in FIG. 23, the opening 310 of the groove 302 is wider than a remainder of the groove 302 and includes curved surfaces 322 that inwardly curve toward the axis 314.

Figure 25:
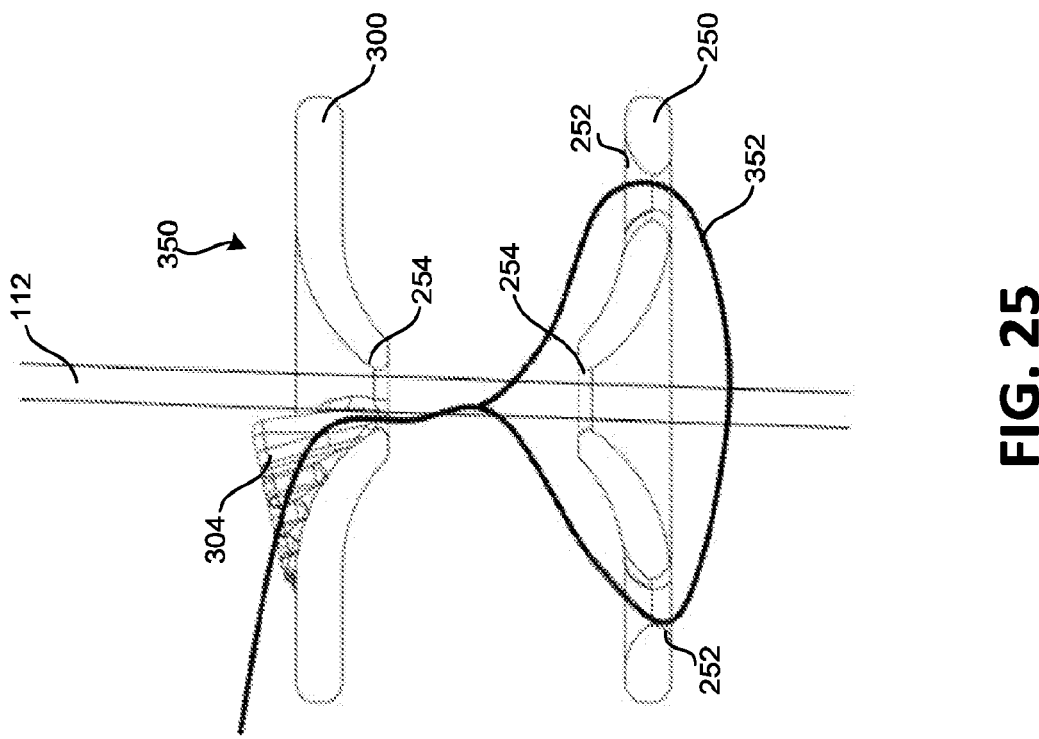
FIG. 25 is a cross-sectional view of a sternal tie assembly including the posterior plug of FIG. 20 and the anterior plug including the cleat of FIG. 22.

FIG. 25 is a cross-sectional view of a sternal tie assembly 350 including the posterior plug 250 of FIG. 20 and the anterior plug 300 including the cleat 304 of FIG. 22. In the implementation shown, the sternal tie 112 passes through the axial bores 254 and the tether 116 forms a loop 352 around the holes 252 of the posterior plug 250, passes through the axial bore 254 of the anterior plug 300 and is secured within the cleat 304 of the anterior plug 300. While not shown in FIG. 25, additional tissue T may be present between the plugs 250, 300.

Figure 26:
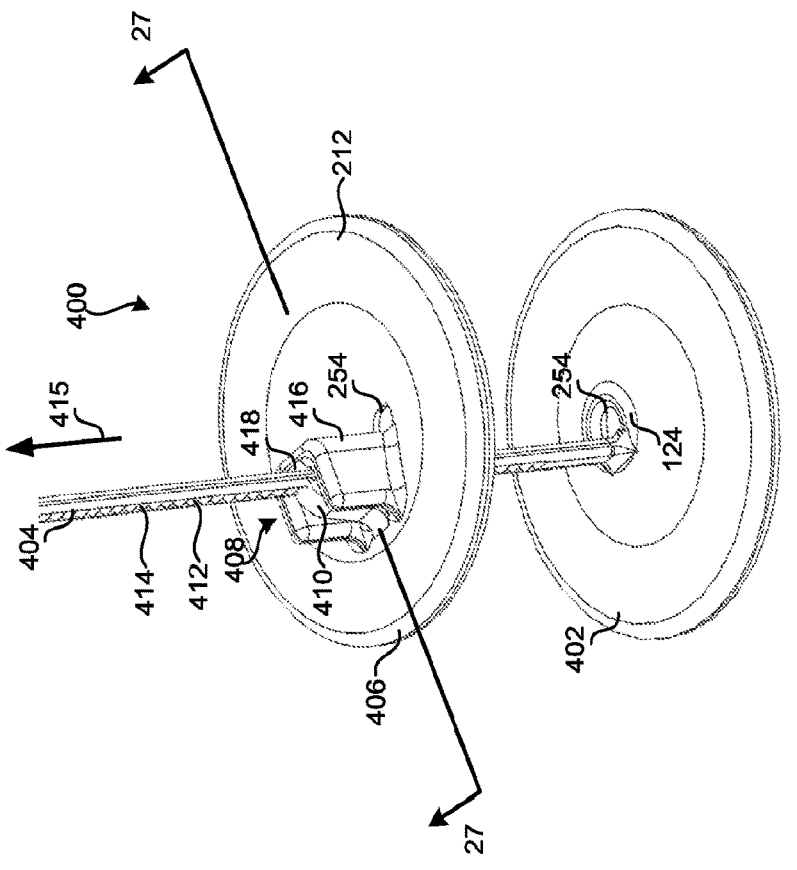
FIG. 26 is an isometric view of another sternal tie assembly including a posterior plug to which a tether extends and an anterior plug including a ratchet.

FIG. 26 is an isometric view of a sternal tie assembly 400 including a posterior plug 402 to which a tether 404 extends and an anterior plug 406 including a ratchet 408. As shown, the ratchet 408 includes a pawl 410 and the tether 404 includes ribs 412 forming grooves 414 that are engageable by the pawl 410 to secure the tether 404 relative to the anterior plug 406. Thus, the interaction between the pawl 410 and the ribs 412 of the tether 404 allows the tether 404 to relatively easily pass through the ratchet 408 in a direction generally indicated by arrow 415 but substantially prevents the tether 404 from slipping backward or otherwise moving in a direction generally opposite that of arrow 415.

The ratchet 408 includes a U-shaped wall 416 that projects from the top surface 212. The U-shaped wall 416 forms a channel 418 and the pawl 410 is at least partially positioned and movable within the channel 418 and the tether 406 extends through the channel 416. In the implementation shown, the tether 116 is integral with the posterior plug 402 and may be made of plastic. However, in other implementations, the tether 404 is coupled to the plug 402 in a different way. For example, the tether 404 may be looped through holes 252 of the posterior plug 404 such the loop pulls relatively evenly on the posterior plug 402 but the tether 404 becomes a single strand before passing through the sternum, manubrium, rib, rib cartilage, intercostal muscle, or other tissue T and/or before being coupled to the needle 114.

Figure 27:
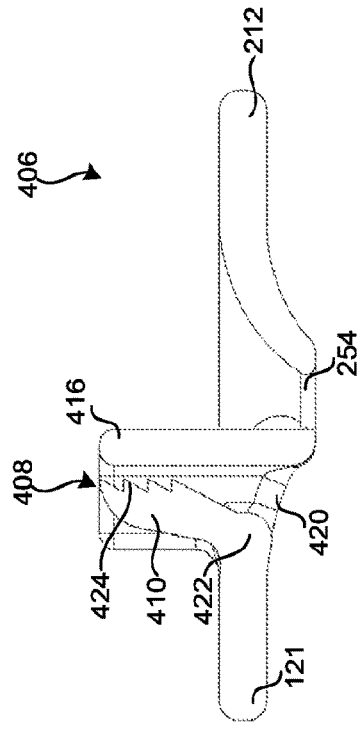
FIG. 27 is a cross-sectional view of the anterior plug of FIG. 26 taken along line 27-27.

FIG. 27 is a cross-sectional view of the anterior plug 406 of FIG. 26 taken along line 27-27. As shown, the plug 406 includes an opening 420 that allows the tether 404 to pass through the ratchet 408 and the pawl 410 is coupled to the head 121 of the plug 406 by a living hinge 422. The pawl 410 also includes a plurality of teeth 424 that are engagable with corresponding grooves 414 of the tether 404.

Figure 28:
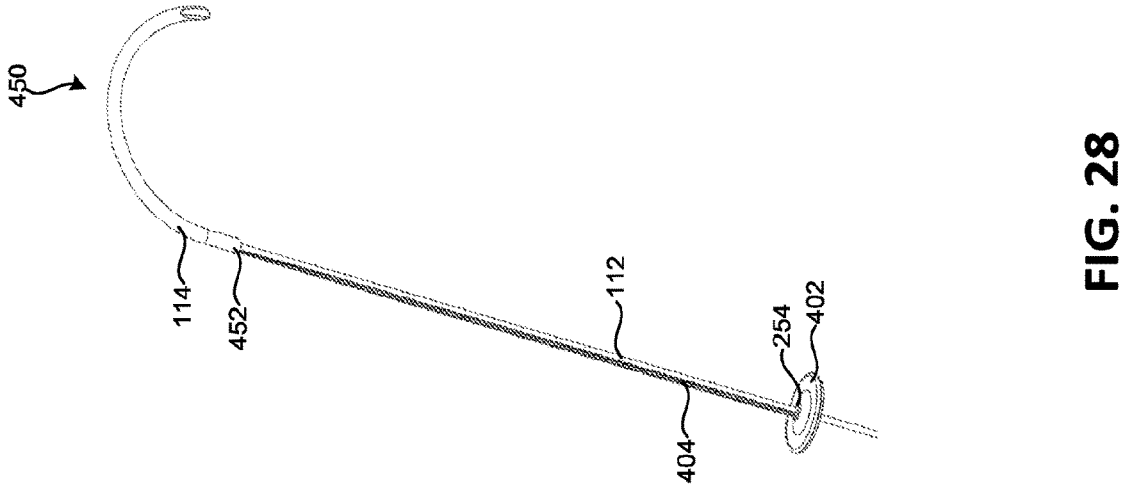
FIG. 28 is an isomeric view of a portion of a tie assembly including the posterior plug and the tether of FIG. 26.

FIG. 28 is an isomeric view of a portion of a tie assembly 450 including the posterior plug 402 and the tether 404 of FIG. 26. The tie assembly 450 also includes the needle 114 and the sternal tie 112 that passes through the axial bore 254 of the plug 402 and is coupled to a proximal end 452 of the needle 114. As shown, the tether 404 is also coupled to the proximal end 452 of the needle 114 and is positioned adjacent to the sternal tie 112. Thus, the tie assembly 450 may be provided preassembled with the tether 404 coupled or otherwise integral with the needle 114 to allow the tether 404 to follow the needle 114 and pass through the bone/tissue.

Figure 29:
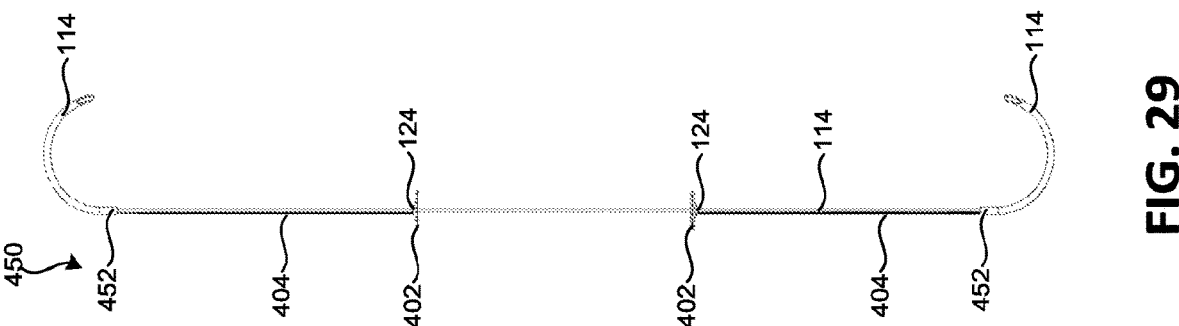
FIG. 29 is a side view of the tie assembly of FIG. 28 showing a pair of needles, two of the posterior plugs, and corresponding tethers coupling the plugs and the needles.

FIG. 29 is a side view of the tie assembly 450 of FIG. 28 showing the pair of needles 114, two of the posterior plugs 402, and corresponding tethers 404 coupling the plugs 402 and the needles 114. As shown, the stems 124 of the plugs 402 face away from one another and toward the proximal end 452 of the corresponding needle 114 to allow the stems 124 to seat within the hole formed by the needle 114.

FIG. 30A is a cross-sectional view of the tie assembly 450 used to close two ends 454 of tissue T together. In the implementation shown, the tethers 404 are secured within the corresponding ratchets 408 and the sternal tie 112 is twisted 122 to bring together and secure the ends 454 relative to one another. Thus, in the implementation shown, the tie 112 may be a wire such as a stainless steel sternal wire.

FIG. 30B is a cross-sectional view of another tie assembly 470 used to close two ends 454 of tissue T together. The tie assembly 470 of FIG. 30B is similar to the tie assembly 450 of FIG. 30A. However, in contrast, the tie assembly 470 of FIG. 30B includes an alternative tie 472 having ends 474, 476 that are secured using a fastener 478. The tie 472 may be made of metal or plastic or any of the other materials disclosed herein and the fastener 476 may be a surgical clip, a crimp etc.

Figure 30C:
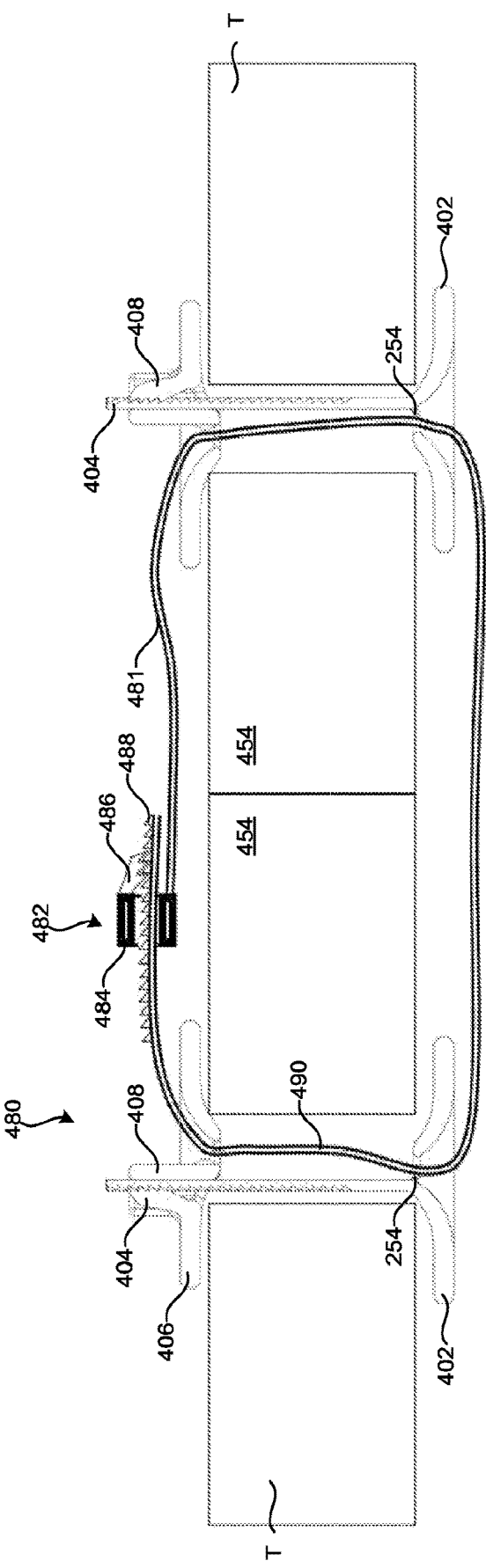
FIG. 30C is a cross-sectional view of another tie assembly used to close two ends of tissue T together.
Figure 31:
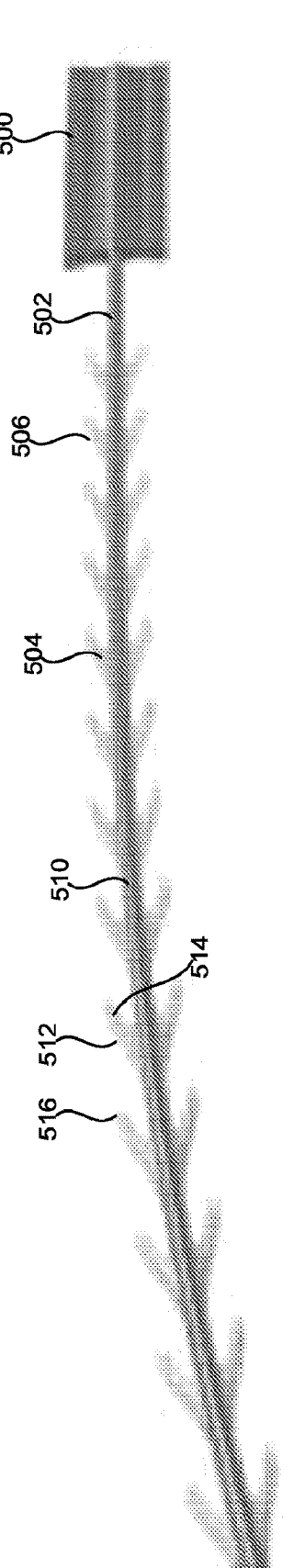
FIG. 31 is an isometric view of another posterior plug to which a tether is coupled.

FIG. 30C is a cross-sectional view of another tie assembly 480 used to close two ends 454 of tissue T together. The tie assembly 480 of FIG. 30C is similar to the tie assembly 470 of FIG. 30B. However, in contrast, the tie assembly 480 of FIG. 30C includes a tie 481 having an alternative fastener 482. The fastener 482 includes a ratchet 484 including a pawl 486 that mates with corresponding ribs 488 that extend from a body 490 of the tie 481. Thus, the fastener 482 is similar to a cable tie. FIG. 31 is an isometric view of another posterior plug 500 to which a tether 502 is coupled. In the implementation shown, the tether 502 includes a plurality of barbs 504 spaced along the tether 502. The barbs 504 are formed in pairs that extend in opposite directions from a body 510 of the tether 502 and rearwardly toward the posterior plug 500. Each of the barbs 504 have tapered surfaces 512, 514 that come together at a tip 516. The forward facing tapered surfaces 512 allow the barbs 504 to relatively easily pass through a hole defined by the anterior plug and the rearward facing tapered surfaces 514 engage against the top surface 212 surrounding the hole of the anterior plug through which the tether 502 passes. Thus, each pair of the barbs 504 has a width that is similar to the diameter of the hole in the anterior plug, so that the tether 502 can relatively easily pass through the anterior plug when being tightened, but the barbs 504 engage against the surface surrounding the hole/the eyelet when the tether 502 is pulled backward, securing the tether 502 and the plugs 500 in place.

Figure 32:
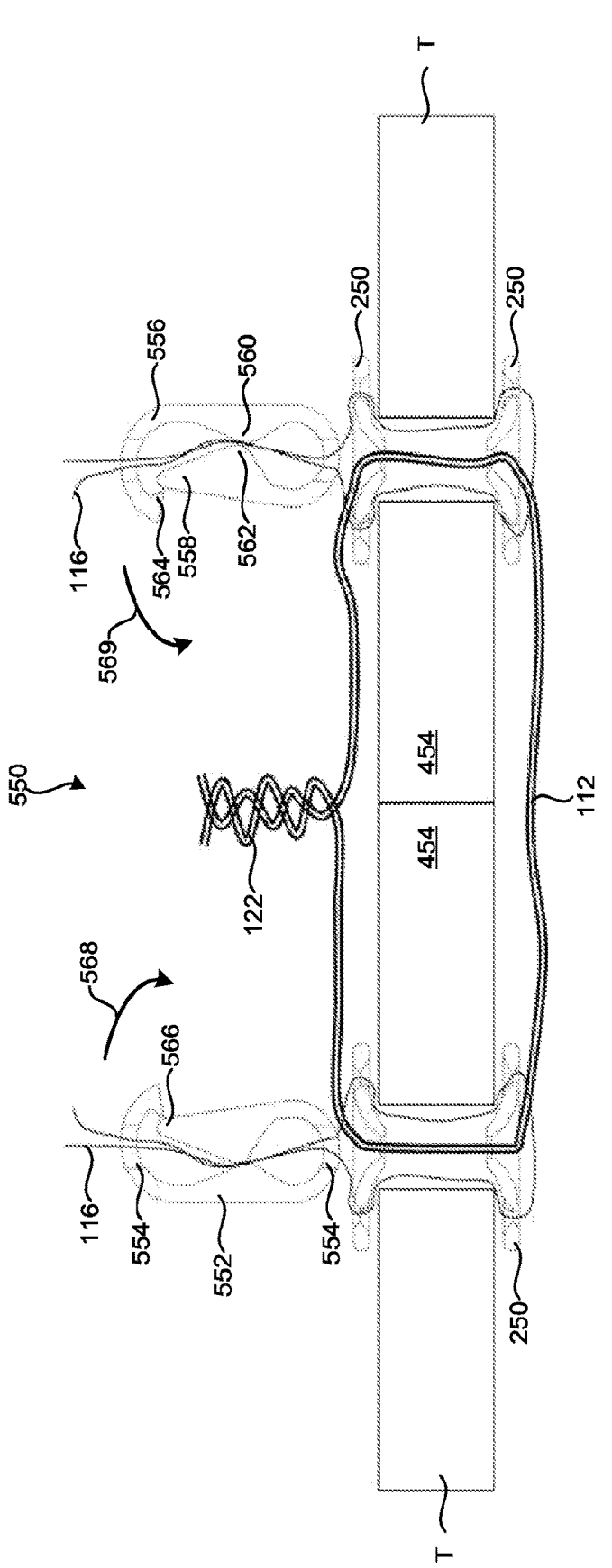
FIG. 32 is a cross-sectional view of another tie assembly used to close two ends of tissue together.

FIG. 32 is a cross-sectional view of another tie assembly 550 used to close two ends 454 of the tissue T together. In the implementation shown, the tie assembly 550 includes the plugs 250 of FIG. 20 with each of the anterior plugs 250 also including a surgical clip 552. The surgical clips 552 may be plastic, metal, biocompatible metal, biocompatible plastic, or bioresorbable and may crimped or snapped onto the corresponding plug 250. The surgical clips 552 may allow the tether 116 to be cut relatively short and the surgical clips 552 may remain in the body after the surgical procedure.

The surgical clip 552 includes openings 554 through which the tether 116 passes and a frame 556 and a moveable arm 558 that is coupled to the frame 556. The frame 556 includes a fixed jaw 560 against which a movable jaw 562 of the arm 558 engages to clip the tether 116 between the jaws 560, 562. Thus, the tether 116 may be held under tension by the surgical clip 552 just above the top surface 212 of the anterior plug 250 without a knot being tied in the tether 116 to potentially reduce time spent during the procedure.

The frame 556 also includes an inward extending protrusion 564 against which an end 566 of the arm 558 engages to secure the arm 558 in the clamped position. The arms 558 may be moved out of engagement with the corresponding protrusion 564 to allow the arms 558 to move in a direction generally indicated by arrows 568, 569, respectively, and open the surgical clip 552.

Figure 33:
FIG. 33 is an isometric view of an assembly used to hold a plurality of the anterior plugs prior to use.

FIG. 33 is an isometric view of an assembly 600 used to hold a plurality of the anterior plugs 250 prior to use. The assembly 600 includes a base 602 having a plurality of spaced apart projections 604 that extend from a top surface 606 of the base 602. In the implementation shown, the projections 604 extend through the corresponding axial bores 254 of the plugs 250. The assembly 600 may also include adhesive 608 on a lower surface 610 of the base 602 that may be used to adhere the assembly 600 to something (e.g., a drape of the patient) during, for example, a surgical procedure in which the plugs 250 are used. A release layer 612 may be disposed overtop of the adhesive 608 and is removable to expose the adhesive 608.

While various embodiments have been described herein, it is understood that variations can be made thereto that are still within the scope of the appended claims.

What is claimed is:

1. A tie assembly comprising:
a needle having a proximal end and a distal end;
a tie extending from the proximal end of the needle;
a plug having an axial bore therethrough, the tie disposed within the bore; and
a tether tethering the plug to the proximal end of the needle,
wherein the plug comprises a post having an axial bore therethrough and a head with an opening in communication with the axial bore of the post, the tie disposed within the bore of the post of the plug, with the head of the plug positioned away from and the post positioned toward the proximal end of the needle along a length of the tie.

2. The tie assembly of claim 1, wherein the needle is hook-shaped.

3. The tie assembly of claim 1, wherein the post of the plug is tapered from a relatively narrow diameter farthest from the head to a relatively wider diameter closer to the head and wherein the tether comprises suture material and wherein the head of the plug includes at least one hole therein, one or more of the holes receiving the suture material to facilitate the tethering of the plug to the proximal end of the needle.

4. The tie assembly of claim 1, the needle being removable from the tie and the tether, and further comprising an additional plug threadable onto an exposed end of the tie upon removal of the needle.

5. A tie assembly comprising:
a needle having a proximal end and a distal end;
a tie extending from the proximal end of the needle;
a plug having an axial bore therethrough, the tie disposed within the bore; and
a tether tethering the plug to the proximal end of the needle,
the needle being removable from the tie and the tether, and further comprising an additional plug threadable onto an exposed end of the tie upon removal of the needle, wherein a head of the additional plug includes at least one tether-receiving groove therein.

6. The tie assembly of claim 5, wherein each tether-receiving groove tapers inwardly from a perimeter of the head toward an axis of the additional plug.

7. The tie assembly of claim 6, wherein each tether-receiving groove further tapers vertically from a bottom toward a top of the head of the additional plug.

8. The tie assembly of claim 5, wherein each tether-receiving groove comprises tapered surfaces that extend inward from a perimeter of the head toward an entrance of a tear-drop shaped opening of the corresponding tether-receiving groove.

9. The tie assembly of claim 5, wherein the at least one tether-receiving groove comprises a pair of tether-receiving grooves.

10. The tie assembly of claim 5, wherein the at least one tether-receiving groove is formed by a cleat.

11. The tie assembly of claim 10, wherein the cleat includes a plurality of inwardly extending teeth.

12. The tie assembly of claim 10, wherein the additional plug has an axial bore and wherein the cleat has an opening adjacent the axial bore.

13. The tie assembly of claim 10, wherein the additional plug has an axial bore and the cleat has a groove that is adjacent to and radially extends from the axial bore.

14. A tie assembly comprising:
a needle having a proximal end and a distal end;
a tie extending from the proximal end of the needle;
a plug having an axial bore therethrough, the tie disposed within the bore; and
a tether tethering the plug to the proximal end of the needle,
the needle being removable from the tie and the tether, and further comprising an additional plug threadable onto an exposed end of the tie upon removal of the needle, wherein the additional plug comprises a ratchet having a pawl and the tether comprises a plurality grooves that are engagable by the pawl.

15. The tie assembly of claim 14, wherein the ratchet comprises a U-shaped wall in which the pawl is movable.

16. The tie assembly of claim 14, wherein the additional plug includes an opening to allow the tether to pass through the additional plug and through the ratchet.

17. The tie assembly of claim 14, wherein the tether is integral with the plug.

18. The tie assembly of claim 14, wherein the pawl comprises a plurality of teeth that are engagable with corresponding grooves of the tether.

19. The tie assembly of claim 18, wherein the tether is coupled with the plug.

20. A tie assembly comprising:
a needle having a proximal end and a distal end;
a tie extending from the proximal end of the needle;
a plug having an axial bore therethrough, the tie disposed within the bore; and a tether tethering the plug to the proximal end of the needle,
the needle being removable from the tie and the tether, and further comprising an additional plug threadable onto an exposed end of the tie upon removal of the needle, wherein the additional plug includes an opening and the tether comprises a plurality of barbs spaced along the tether and engagable against a surface of the additional plug surrounding the opening.

21. A tie assembly comprising:
a needle having a proximal end and a distal end;
a tie extending from the proximal end of the needle;
a plug having an axial bore therethrough, the tie disposed within the bore; and
a tether tethering the plug to the proximal end of the needle,
the needle being removable from the tie and the tether, and further comprising an additional plug threadable onto an exposed end of the tie upon removal of the needle, wherein the additional plug includes a surgical clip to secure the tether relative thereto.

22. A tie assembly comprising:

a needle having a proximal end and a distal end;

a tie extending from the proximal end of the needle;

a plug having an axial bore therethrough, the tie disposed within the bore; and a tether tethering the plug to the proximal end of the needle, further comprising a base having a plurality of spaced apart projections, and further comprising a plurality of additional plugs each having an axial bore through which a corresponding projection extends.

23. The tie assembly of claim 22, wherein the plug comprises a post having an axial bore therethrough and a head with an opening in communication with the axial bore of the post, the tie disposed within the bore of the post of the plug, with the head of the plug positioned away from and the post positioned toward the proximal end of the needle along a length of the tie.

24. The tie assembly of claim 22, further comprising at least one of adhesive on a surface of the base opposite the projections or a release label disposed over the adhesive.

* * * * *